US012767920B2

(12) United States Patent
Lim et al.

(10) Patent No.: US 12,767,920 B2
(45) Date of Patent: Oct. 20, 2026

(54) MULTIPLE INCUBATOR CELL CULTURE SYSTEM WITH ATMOSPHERIC REGULATION OPERATED BY AN INTEGRATED CONTROL SYSTEM

(71) Applicant: XCELL BIOSCIENCES, INC., San Francisco, CA (US)

(72) Inventors: James Lim, Oakland, CA (US); Brian Feth, San Francisco, CA (US); Becky Rutherford, San Francisco, CA (US); Janette Trang Phi, Los Altos Hills, CA (US); Nicholas George Erndt, Los Altos Hills, CA (US)

(73) Assignee: XCELL BIOSCIENCES, INC., San Francisco, CA (US)

( * ) Notice: Subject to any disclaimer, the term of this patent is extended or adjusted under 35 U.S.C. 154(b) by 0 days.

(21) Appl. No.: 18/313,697

(22) Filed: May 8, 2023

(65) Prior Publication Data

US 2024/0002774 A1 Jan. 4, 2024

Related U.S. Application Data

(63) Continuation of application No. 16/967,238, filed as application No. PCT/US2019/016505 on Feb. 4, 2019, now abandoned.

(Continued)

(51) Int. Cl.

*C12M 1/00* (2006.01)
*C12M 1/04* (2006.01)

(Continued)

(52) U.S. Cl.

CPC ............ *C12M 41/14* (2013.01); *C12M 1/005* (2013.01); *C12M 1/04* (2013.01); *C12M 1/34* (2013.01);

(Continued)

(58) Field of Classification Search

CPC ........ C12M 41/14; C12M 1/005; C12M 1/04; C12M 1/34; C12M 1/36; C12M 23/44;

(Continued)

(56) References Cited

U.S. PATENT DOCUMENTS

2003/0092178 A1 5/2003 Yerden
2005/0158701 A1 7/2005 West (Continued)

FOREIGN PATENT DOCUMENTS

WO WO-2009135206 A1 11/2009
WO WO-2010099539 A1 9/2010

(Continued)

OTHER PUBLICATIONS

Butcher et al.: A tense situation: forcing tumour progression, Nat Rev Cancer. Feb. 2009, 9(2): 108-122. doi: 10.1038/nrc2544.

(Continued)

*Primary Examiner* — William H. Beisner
*Assistant Examiner* — Danielle B Henkel
(74) *Attorney, Agent, or Firm* — Snell & Wilmer, L.L.P.; April Wurster

(57) ABSTRACT

Embodiments of a cell culture incubator system provided herein have two or more individual incubators and atmospheric regulation system configured to regulate atmospheric conditions within the environmental chamber of each individual incubator. The atmospheric regulation system has a single integrated controller system that controls atmospheric regulation of each of the individual incubators independently of the one or more other individual incubators. Atmospheric conditions within each of the individual incubators include at least the oxygen level and the total gas pressure, which are regulated independently of each other.

22 Claims, 14 Drawing Sheets

Related U.S. Application Data

(60) Provisional application No. 62/626,364, filed on Feb. 5, 2018.

(51) Int. Cl.
*C12M 1/34* (2006.01)
*C12M 1/36* (2006.01)
*C12M 3/00* (2006.01)
*C12M 3/06* (2006.01)

(52) U.S. Cl.
CPC .............. *C12M 1/36* (2013.01); *C12M 23/44* (2013.01); *C12M 27/16* (2013.01); *C12M 41/34* (2013.01); *C12M 41/40* (2013.01); *C12M 41/48* (2013.01)

(58) Field of Classification Search
CPC ...... C12M 27/16; C12M 41/34; C12M 41/40; C12M 41/48
See application file for complete search history.

(56) References Cited

U.S. PATENT DOCUMENTS

| | | | | |
|---|---|---|---|---|
| 2005/0213374 | A1 | 9/2005 | Xu et al. | |
| 2005/0255583 | A1* | 11/2005 | DePaola | C12M 35/06 435/286.2 |
| 2008/0282653 | A1* | 11/2008 | Tempelman | C25B 9/73 55/385.2 |
| 2009/0053813 | A1 | 2/2009 | Evans | |
| 2009/0305380 | A1 | 12/2009 | Ragsdale | |
| 2011/0060463 | A1* | 3/2011 | Selker | G05B 23/0221 700/266 |
| 2014/0133702 | A1 | 5/2014 | Zheng et al. | |
| 2014/0273211 | A1 | 9/2014 | Slukvin et al. | |
| 2014/0286910 | A1 | 9/2014 | Tankovich et al. | |
| 2014/0287509 | A1 | 9/2014 | Sharei et al. | |
| 2014/0370598 | A1 | 12/2014 | Colton et al. | |
| 2015/0010517 | A1 | 1/2015 | Chapman | |
| 2016/0113968 | A1 | 4/2016 | Hung | |
| 2016/0193605 | A1 | 7/2016 | Sharei et al. | |
| 2016/0222353 | A1 | 8/2016 | Yang et al. | |
| 2016/0251620 | A1 | 9/2016 | Gobbi | |
| 2016/0289635 | A1 | 10/2016 | Sasai et al. | |
| 2017/0007677 | A1 | 1/2017 | Ueda | |
| 2017/0009204 | A1 | 1/2017 | Gerecht et al. | |
| 2017/0073628 | A1 | 3/2017 | Zander et al. | |
| 2017/0105984 | A1 | 4/2017 | Saya et al. | |
| 2017/0114316 | A1 | 4/2017 | Newstrom et al. | |
| 2017/0121677 | A1 | 5/2017 | Colton et al. | |
| 2017/0130198 | A1 | 5/2017 | Tyvoll et al. | |
| 2021/0032587 | A1* | 2/2021 | Lim | C12M 27/16 |

FOREIGN PATENT DOCUMENTS

| | | | |
|---|---|---|---|
| WO | WO-2012098380 | A1 | 7/2012 |
| WO | WO-2014086984 | A1 | 6/2014 |
| WO | WO-2014117021 | A2 | 7/2014 |
| WO | WO-2016064757 | A1 | 4/2016 |
| WO | WO-2016070136 | A1 | 5/2016 |
| WO | WO-2016077761 | A1 | 5/2016 |
| WO | WO-2016115179 | A1 | 7/2016 |
| WO | WO-2016168687 | A1 | 10/2016 |
| WO | WO-2017008063 | A1 | 1/2017 |
| WO | WO-2017041051 | A1 | 3/2017 |
| WO | WO-2017070337 | A1 | 4/2017 |
| WO | WO-2017123663 | A1 | 7/2017 |
| WO | WO-2017172638 | A1 | 10/2017 |
| WO | WO-2017192785 | A1 | 11/2017 |
| WO | WO-2019126146 | A1 | 6/2019 |

OTHER PUBLICATIONS

Carey et al.: Mechanobiology of tumor invasion: engineering meets oncology, Crit Rev Oncol. Hematol. 83(2):170-183 (2012).
PCT/US2019/016505 International Search Report and Written Opinion dated Jun. 27, 2019.
Salvagiotto et al. A Defined, Feeder-Free, Serum-Free System to Generate In Vitro Hematopoietic Progenitors and Differentiated Blood Cells from hESCs and hiPSCs, PLoS One, Mar. 2011, 6(3): e17829, 9 pages.
Schwartz et al.: Exposure of Human Vascular Endothelial Cells to Sustained Hydrostatic Pressure Stimulates Proliferation Involvement of the aV Integrins, Circ. Res. 84:315-322 (1999).
Sullivan et al.: Hypoxia-induced resistance to anticancer drugs is associated with decreased senescence and requires hypoxia-inducible factor-1 activity, Mol Cancer Ther. 7(7):1961-73 (2008).
Takahashi, et al.: A developmental framework for induced pluripotency. The Company of Biologist 2015, 142, pp. 3274-3285.
Wang et al. Targeting HIF1α eliminates cancer stem cells in hematological malignancies. Cell Stem Cell 8(4):399-411 (2011).

* cited by examiner

MULTIPLE INCUBATOR CELL CULTURE SYSTEM WITH ATMOSPHERIC REGULATION OPERATED BY AN INTEGRATED CONTROL SYSTEM

CROSS-REFERENCE TO RELATED APPLICATIONS

This application is a continuation of U.S. application Ser. No. 16/967,238 filed Aug. 4, 2020, which claims priority to 371 International Application No. PCT/US19/16505, filed Feb. 4, 2019, which application claims priority to U.S. Provisional Application No. 62/626,364, filed on Feb. 5, 2018, which is incorporated herein by reference in its entirety.

TECHNICAL FIELD

This application is directed to technologies for the expansion of cell populations that may be used in research or human therapy, such as for use in immunotherapy. In particular, the technologies relate to methods of optimizing the therapeutic potential of these populations by way of regulating environmental variables within a cell culture incubator.

BACKGROUND

The use of cells, such as immune system cells, tumor cells, and stem cells, for research, diagnostic, drug screening, or therapeutic purposes is an area of active interest, and accordingly, there is a need for methods to isolate and expand high quality cell populations for these purposes. At the same time, there is also a growing awareness that the physical structure and atmospheric conditions of a cell culture environment can have marked effects on cellular processes and many aspects of phenotypic expression.

In a conventional cell culture incubator, cells are in a liquid medium that interfaces with the atmospheric environment within the incubator. The incubator-internal atmospheric environment is generally very similar to the external atmospheric environment, with the exception of an increased level of carbon dioxide, whose purpose is to buffer the cell culture medium. Otherwise, absent manipulation, the oxygen level and total atmospheric pressure level are typically near their respective ambient levels.

In contrast, local compartments in the body are commonly hypoxic and/or hyperbaric. Hypoxia is known as an influencing atmospheric factor with regard to a host of effects on particular types of cells, as significantly mediated by hypoxia-inducible factors. The effects of total atmospheric pressure on cells are less well understood than the effects of hypoxia, at least in part, because while it is relatively easy to create different levels of oxygen within an incubator environment, in contrast, available cell incubator options that can controllably vary the internal atmospheric pressure are scarce. Accordingly, it is appropriate to regard oxygen and pressure as atmospheric variables that may have significant effects on the performance and phenotypic aspects of cells in culture.

There is a need in the market for systems and methods that allow fine control of the composition and pressure of the atmosphere within a cell culture environment, and that also provide for scalability of cell culture volumes, particularly for therapeutic use.

INCORPORATION BY REFERENCE

Each patent, publication, and non-patent literature cited in the application is hereby incorporated by reference in its entirety as if each was incorporated by reference individually.

SUMMARY OF THE TECHNOLOGY

Embodiments of a cell culture technology disclosed herein relate to a cell culture incubator system having multiple incubators under the control of a single integrated controller system; embodiments further relate to methods of operating such a multi-incubator cell culture system.

Embodiments of a multi-incubator cell culture system, as provided herein, include two or more individual incubators (each individual incubator including an environmental chamber) and an atmospheric regulation system configured to regulate atmospheric conditions within the environmental chamber of each individual incubator, the atmospheric conditions including, in particular, an oxygen level and a total gas pressure level. Unless otherwise specified, "pressure", as used herein, refers to the total atmospheric pressure (the sum of all partial pressures of all gases) within an environmental chamber. The atmospheric regulation system is configured to regulate the oxygen level and the total gas pressure within each incubator independently of each other. The atmospheric regulation system has a single integrated controller system that is configured to command atmospheric regulation of each of the individual incubators independently of the atmospheric regulation of the one or more other individual incubators.

In particular embodiments of the of the multi-incubator cell culture system, the integrated controller system includes a single master controller operably linked to each of the individual incubators and two or more subcontrollers, each subcontroller dedicated, respectively, to one of the two or more individual incubators. The master controller is configured to deliver atmospheric condition set point commands to each of the two or more subcontrollers, and each subcontroller, in turn, regulates the atmospheric regulation system of the individual incubator to which it is dedicated, in accordance with the atmospheric condition set points commands of the master controller. In some embodiments of the integrated controller system, each of the subcontrollers may be positioned within or proximate the incubator to which it is dedicated.

Embodiments of the integrated controller system are considered "integrated" for at least two reasons. First, control over atmospheric conditions within the environmental chamber of each of the multiple incubators is exerted by the combined or concerted (thus "integrated") action of the single master controller and the particular subcontroller that is dedicated to each individual incubator. Second, although regulation of atmospheric conditions within each of the individual incubators is independent of the regulation of atmospheric conditions of other incubators, the control of atmospheric conditions within the multiple incubators, collectively, is integrated by the centrality or dominance of control by way of the single master controller.

Embodiments of the integrated controller system are configured to regulate atmospheric conditions within each incubator by way of an atmospheric regulation system, as described herein. The "configuration" of the integrated controller system refers to the firmware and operating software of the master controller and subcontrollers by which control is exerted, and through which atmospheric sensor data from within the multiple incubators is processed and responded to. Firmware and software may be of any suitable brand or type, and configured into any suitable arrangement, that implements rules or responses related to atmospheric condition set points and feedback to atmospheric sensory data, as described in the context of methods of operational control, as described herein.

"Set point" refers to a target value toward which embodiments of the multi-incubator cell culture system are configured to drive an atmospheric condition level. An actual atmospheric condition, as measured in an environmental chamber may be either within compliance- or out of compliance with the set point. If out of compliance, the atmospheric condition may be either below or above the set point. Responses of the integrated controller system will vary according to whether the atmospheric condition is below or above the set point. Responses of the system may also vary according to the particulars of the gas or general atmospheric conditions being dealt with, and system responses may also vary in accordance with the performance particulars of the atmospheric condition sensors deployed within the multi-incubator system provided herein.

In typical embodiments of the integrated controller system, each subcontroller includes two or more atmospheric condition regulation modules, these modules including at least an oxygen module and a pressure module. In some related embodiments, each subcontroller may include one or more further atmospheric condition regulation modules, these further modules may include a carbon dioxide module, a temperature module, or a humidity module.

In some embodiments of the integrated controller system, the master controller is configured to request and receive sensor data from any of the two or more subcontrollers, the sensor data including data from any sensed atmospheric condition from any of the two or more individual incubators. Further, in some embodiments, the master controller, in response to sensor data received from a subcontroller, is configured to send atmospheric regulation commands to an atmospheric regulation module within any of the two or more individual incubators.

In some embodiments of the integrated controller system (of the multi-incubator cell culture system) being configured to operate each of the individual incubators independently of the one or more other individual incubators includes being configured to be able to operate two or more of the individual incubators in parallel with respect to the atmospheric conditions within the individual incubators. In some embodiments, the integrated controller system 40 is configured to operate all of the individual incubators in parallel. "Parallel", as used herein, refers to operation of individual incubators in a manner where the atmospheric conditions (e.g., oxygen level, pressure, carbon dioxide, temperature, humidity) are alike in the at least two incubators over the duration of a cell culture time course. However, being configured to operate each of the individual incubators independently of the one or more other individual incubators may also include the integrated controller system being configured to be able to operate the individual incubators such that at least one of the individual incubators differs from at least one other individual incubator (and thus is non-parallel) with respect to the atmospheric conditions within the other individual incubators.

Operating individual incubators in parallel or non-parallel workflows each have their various uses and advantages. Non-parallel work flows may be effectively applied, for example, to systematic experimental testing of various atmospheric condition regimes for optimizing any particular kind of cell culture deliverable. Parallel workflows may be effectively applied, for example, to scaling up workflow or process volumes to achieve a particular cell culture deliverable in a manufacturing context, when optimal atmospheric conditions are already known.

In some embodiments of the atmospheric regulation system of the multi-incubator cell culture system (wherein the integrated controller system includes an oxygen module and a pressure module) the atmospheric regulation system further includes (a) an oxygen sensor configured to measure the oxygen level within the environmental chamber and to convey an oxygen level signal to the oxygen module, (b) a pressure sensor configured to measure the total gas pressure within the environmental chamber and to convey a pressure level signal to the pressure module, and (c) a gas flow system having multiple gas sources flowably connected to the environmental chamber, these gas sources including a nitrogen source, a carbon dioxide source, and an air source, wherein gas flow from each source, respectively, is regulated by the integrated controller system. The air source may also be understood as an oxygen source, inasmuch as it contains oxygen.

In such an embodiment, the integrated controller system is configured to regulate each of an oxygen level and a total gas pressure within the environmental chamber, and the integrated controller system is configured to (a) provide a hypoxic oxygen set point to the oxygen module, and (b) provide a hyperbaric total gas pressure set point to the atmospheric regulation system. Further in such an embodiment, the regulation of the oxygen level to the hypoxic level set point prevails despite an oxygen partial pressure-increasing effect of the hyperbaric pressure condition, per the positive pressure set point.

In some embodiments of the atmospheric regulation system of the multi-incubator cell culture system, the master controller is configured such that when an atmospheric condition within an environmental chamber of one of the incubator chambers is sensed as being out of set point compliance, the master controller drives, by way of the gas flow system, a transition of the atmospheric condition within the environmental chamber toward the set point, said transition mediated by the subcontroller dedicated to the individual incubator.

However, in some embodiments of the atmospheric regulation system, when an atmospheric condition within an environmental chamber of one of the incubator chambers is sensed as being in-compliance with the atmospheric condition set point, the subcontroller dedicated to the incubator can be operable to control the gas flow system without an ongoing atmospheric set point command from the master controller.

In some embodiments of the atmospheric regulation system of the multi-incubator cell culture system, each of the individual incubators includes at least two atmospheric sensors, these two sensors including an oxygen sensor and an atmospheric (total gas) pressure sensor, these sensors being disposed within the environmental chamber and being configured to transmit sensed data to the subcontroller of the integrated controller system. In such embodiments, the subcontroller of the integrated controller system may be configured to transmit sensed data to the master controller. Further, the subcontroller of the integrated controller system may be configured to transmit sensed data to the master controller at a rate that is controllably variable.

In some embodiments of the multi-incubator cell culture system, the integrated controller system of at least one of the multiple incubators includes one or more analytic modules configured to non-invasively capture analytic data informative of an aspect of performance of a cell population being cultured within a cell culture vessel disposed within the incubator. Non-invasive, in this sense, refers to the absence of physical intrusion into the cell culture vessel.

In some embodiments, the analytic module of the integrated controller system of at least one of the multiple incubators includes an impedance mapping module configured to receive grid site-tagged impedance data transmitted from an electrode mapping grid included within the cell culture surface of a cell culture vessel disposed within the cell culture incubator, and the mapped impedance data are processable into a map of cellular attachment to the cell culture surface of the cell culture vessel.

In some embodiments, the analytic module of the analytic module of the integrated controller system of the at least one of the multiple incubators comprises an optical module configured to receive optical data captured from the cell culture vessel within the incubator, and wherein the optical data are processable into a measure of cellular presence within the cell culture vessel. In a particular embodiment, optical module is configured to receive optical data that is site-tagged, the optical data being transmitted from an optical mapping grid included within a cell culture surface of the cell culture vessel disposed within the cell culture incubator, and wherein the mapped optical data are processable into a map of cellular presence on the cell culture surface of the cell culture vessel.

In some embodiments of the multi-incubator cell culture system, at least one of the multiple incubators includes a current delivery module within the integrated control system that is configured to be able to transmit electrical current by way of an electrode array disposed within a cell culture surface of a cell culture vessel housed within the cell culture incubator, the transmitted current being effective to electroporate a cell adhering to the cell culture surface.

In some embodiments of the multi-incubator cell culture system, at least one of the individual incubators is sized and configured to accommodate a cell culture bag rocker device and a cell culture bag of at least 1-liter volume disposed thereon. And in some embodiments of the multi-incubator cell culture system, at least one of the individual incubators is sized and configured to accommodate a cell flask orbiter and a cell culture flask of at least 500 ml capacity thereon.

Embodiments of the multi-incubator cell culture system typically include between two and six or more individual incubators arranged and configured in various ways. In one embodiment, the individual incubators are configured to be individually freestanding, arranged, for example, on a bench, shelf, or rack. In one embodiment, the individual incubators are configured to be stackable, such that each individual incubator is positioned over and/or under another individual incubator. In one embodiment, by way of example, a set of six individual incubators is arranged as two side-by-side stacks of three incubators. In a particular example, a multi-incubator cell culture system may be configured as a set of two individual incubators arranged within a single housing.

The number of incubators included in an embodiment of the multi-incubator system, as provided herein, is not limited by the conceptual foundation of the integrated controller system, and could well accommodate more than six individual incubators, although there may be practical constraints at some point in terms of cable arrangements, for example. Further, embodiments of the integrated controller system could include a higher level of master controller, or it could include multiple multi-incubator systems linked together.

DETAILED DESCRIPTION

Figure 1:
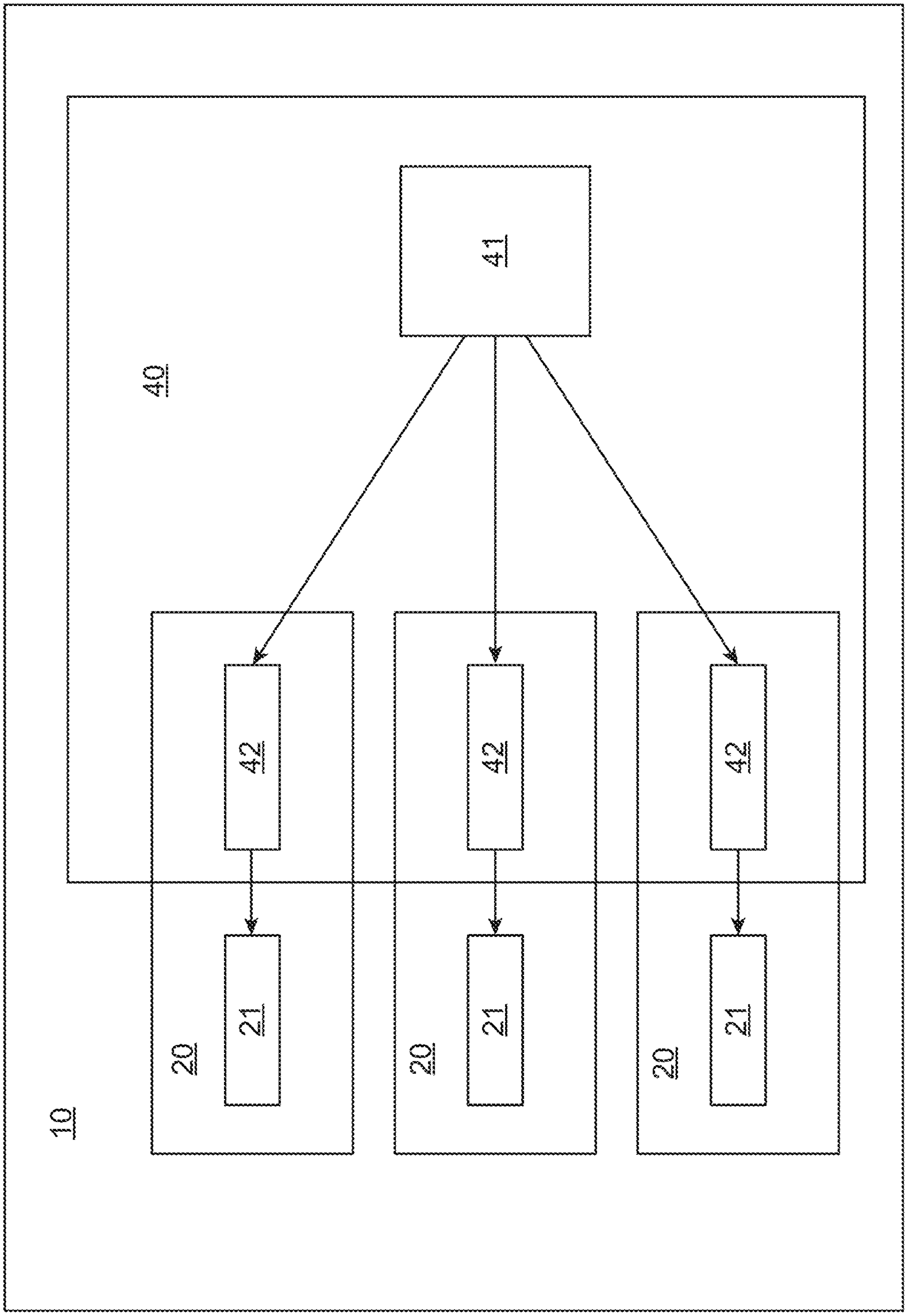
FIG. 1 shows a multi-incubator cell culture system embodiment, with particular attention to its single integrated controller system.

Pressure and Oxygen: Roles in the In Vitro Environment and Modulating the Biology of Cells Embodiments of the technology include methods of modulating aspects of cellular biology by way of regulating the gaseous or atmospheric environment within a cell culture incubator. Cellular responses to manipulation of the gaseous environment, merely by way of example, may include (1) the modulation of expressed cellular phenotypes with respect to cellular potency-level, particularly with regard to the continuum ranging between pluripotent and differentiated states, and (2) the cellular amenability to accepting transfective bioactive agents. Regulating the gaseous environment (including total atmospheric pressure and oxygen level) within a cell culture incubator may be directed toward holding a particular condition in a steady state, and it may also be directed toward providing a dynamic state, in which aspects of the gaseous environment change during the course of a cell culture duration.

Gaseous environment parameters include the total atmospheric pressure as well as the partial pressure of individual gases. Of the various individual gases included in the cell culture environment, embodiments of the technology described here relate particularly to oxygen, and more particularly to low-oxygen or hypoxic conditions. Regarding total atmospheric pressure, biological responses described herein relate primarily to the effects of an atmospheric pressure that is elevated above the ambient atmospheric pressure. Total gas pressure values are typically recited in terms of the pounds/square inch (PSI), which should be understood as the PSI level above ambient atmospheric pressure.

Oxygen levels are typically referred to in terms of a concentration % value, i.e., the relative amount of oxygen present with respect to all gases present within a given volume, regardless of the summed total atmospheric pressure of all gases present. A parameter thought be more biologically relevant than "concentration %" is the partial pressure of oxygen, i.e., the amount of oxygen present per unit volume, in absolute terms, regardless of the relative presence of other gases. However, oxygen level is commonly recited as a concentration % value, and instruments typically display oxygen level as a concentration % value. Accordingly, a parameter term generally used in this application is simply oxygen concentration %.

As noted above, embodiments of the disclosed technology independently regulate oxygen level and total gas pressure within the confines of a cell culture incubator chamber. A term which incorporates both variables, the "O-P condition"; this term refers to a condition that is defined by the combination of the two variable atmospheric parameters (oxygen level and total gas pressure). Any terminology that defines each parameter, respectively can be used to identify the O-P condition. For example, oxygen level may be defined in terms of concentration (relative % of total gas) or in terms of partial pressure (absolute level of oxygen per unit volume). By way of a specific example, an O-P condition could be defined as "3% oxygen-3 PSI".

Cell culture "duration" or "course", as used herein, are terms that refer to a length of time during which a particular population of cells, a subpopulation of cells, a single cell, or descendants of any of the foregoing are in culture within an incubator enabled to regulate the gas composition to which cells are exposed. A cell culture duration is typically at least a day, and typically can range from periods of several days, several weeks, and even several months, during which time the cultured cells can be cultured under different conditions, and be subject to one or more workflows during which cells are subjected to different sets of conditions, in various orders, to one or more particular ends.

Cell populations, as subjected to methods provided herein, typically are outside the body, in vitro, within a cell culture incubator. Cell culturing, thus, refers to growing or maintaining cells within an incubator. Cultured cells may also live without dividing, in which case cells can be said to be maintained in cell culture.

The whole of a cell culture environment within an incubator includes many factors, merely by way of example, the composition of the liquid cell culture medium and bioactive agents included therein, surfaces and structures with which cells engage, temperature, and atmospheric conditions external to the liquid. Embodiments of methods provided herein, focus on regulating the gaseous composition and the total gas pressure, as noted above in the description of the O-P condition. The cell culture environment also includes the composition of the liquid cell culture medium, including organic and inorganic compounds, as well as particular bioactive agents. Bioactive agents are compounds that are not metabolic fuel or nutritional, but rather have biological effects that follow from their informational or directive nature, as typically mediated by physical or chemical interaction with molecules of the target cell. The cell culture environment may further include physical or chemical aspects of the surfaces that cells contact. The cell culture environment may further include any structural features with which cultured cells may interact, for example, features that provide a 3D structural context. The cell culture environment may also include interactive relationships between cells or among cell populations. The cell culture environment may further include electrical engagement of cells, for example electrical current as transmitted through the liquid medium or through solid structures which cells may contact.

Multi-Incubator Cell Culture System

Figure 2:
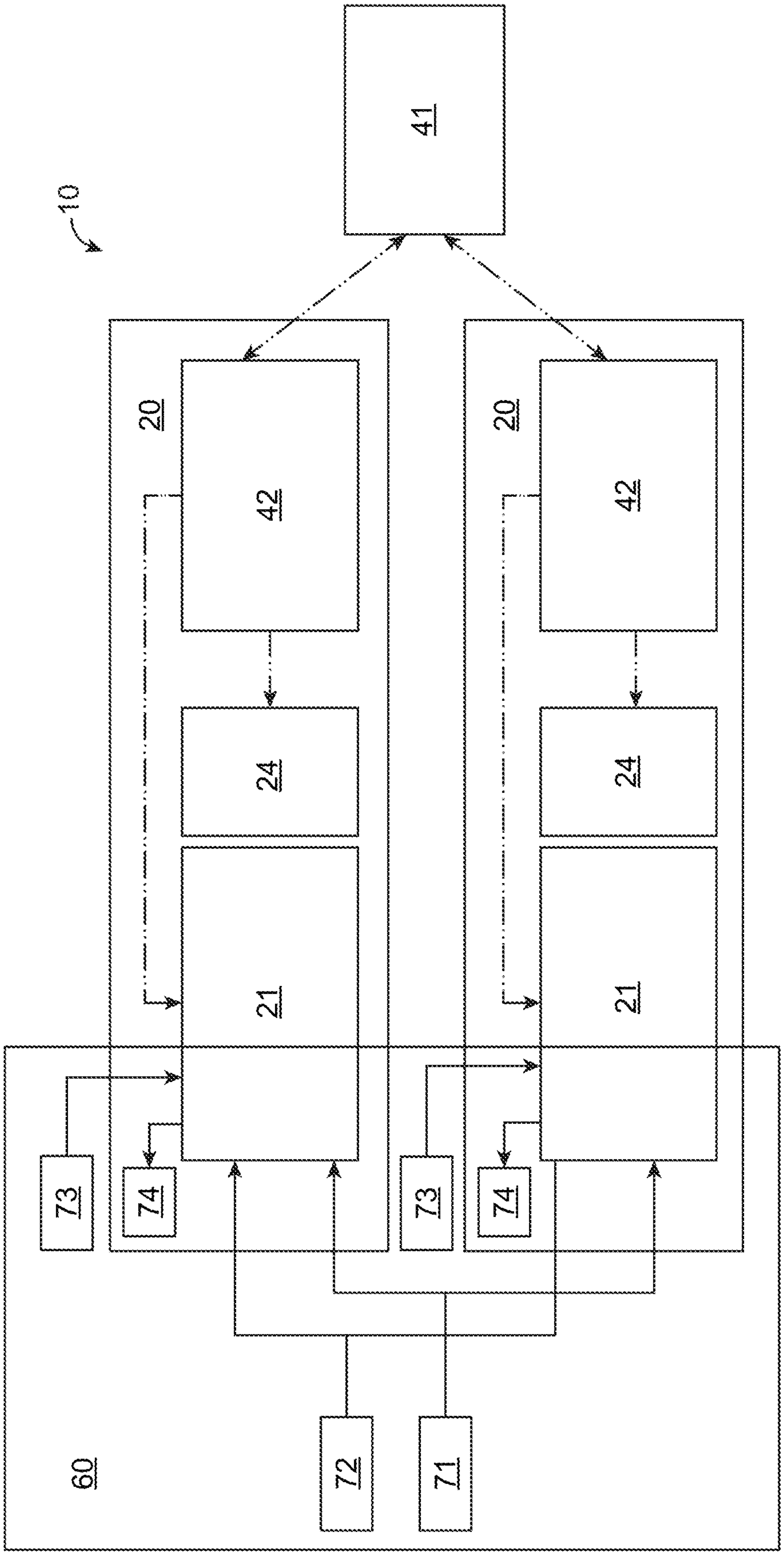
FIG. 2 shows of a multi-incubator cell culture system embodiment under the control of a single integrated controller system, with particular attention to a gas flow system.
Figure 3:
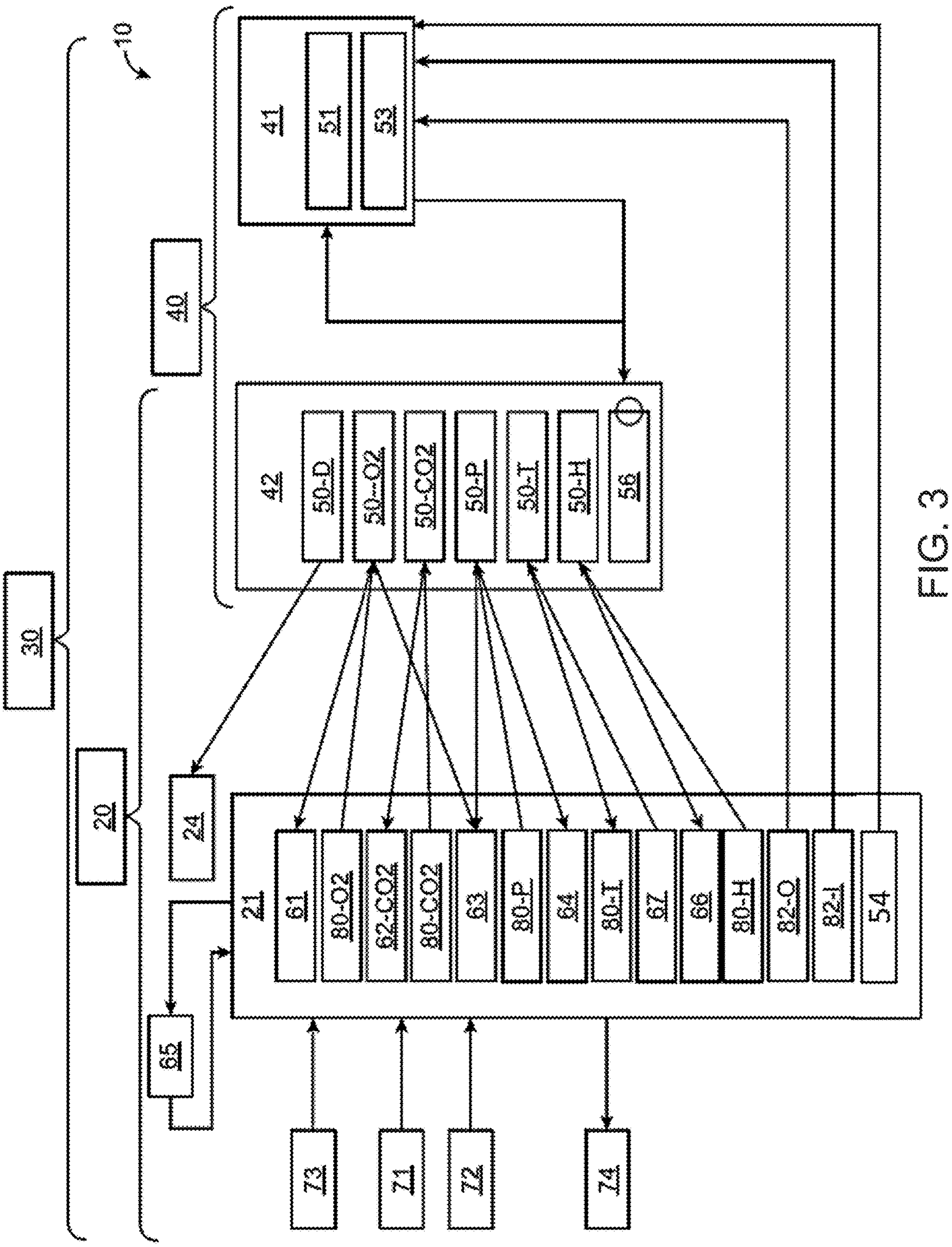
FIG. 3 shows an isolated single incubator member of a multi-incubator cell culture system embodiment under the control of a single integrated controller system, with particular attention to its atmospheric regulation system and hardware features.

FIGS. 1-4 all depict embodiments of a multi-incubator cell culture system 10, as provided herein, showing particular aspects of the system, and with varying degrees of detail. Multi-incubator cell culture system 10, as indicated by the term, has more than one incubator 20, but for clarity, FIG. 3 shows a single incubator to allow for depiction of a greater amount of detail. FIGS. 5-12 show various superficial views of multi-incubator cell culture system 10, showing various configurations according the number and arrangement of multiple incubators, as well as interior views of the cell culture chamber and cell culture vessels disposed therein.

Figure 13:
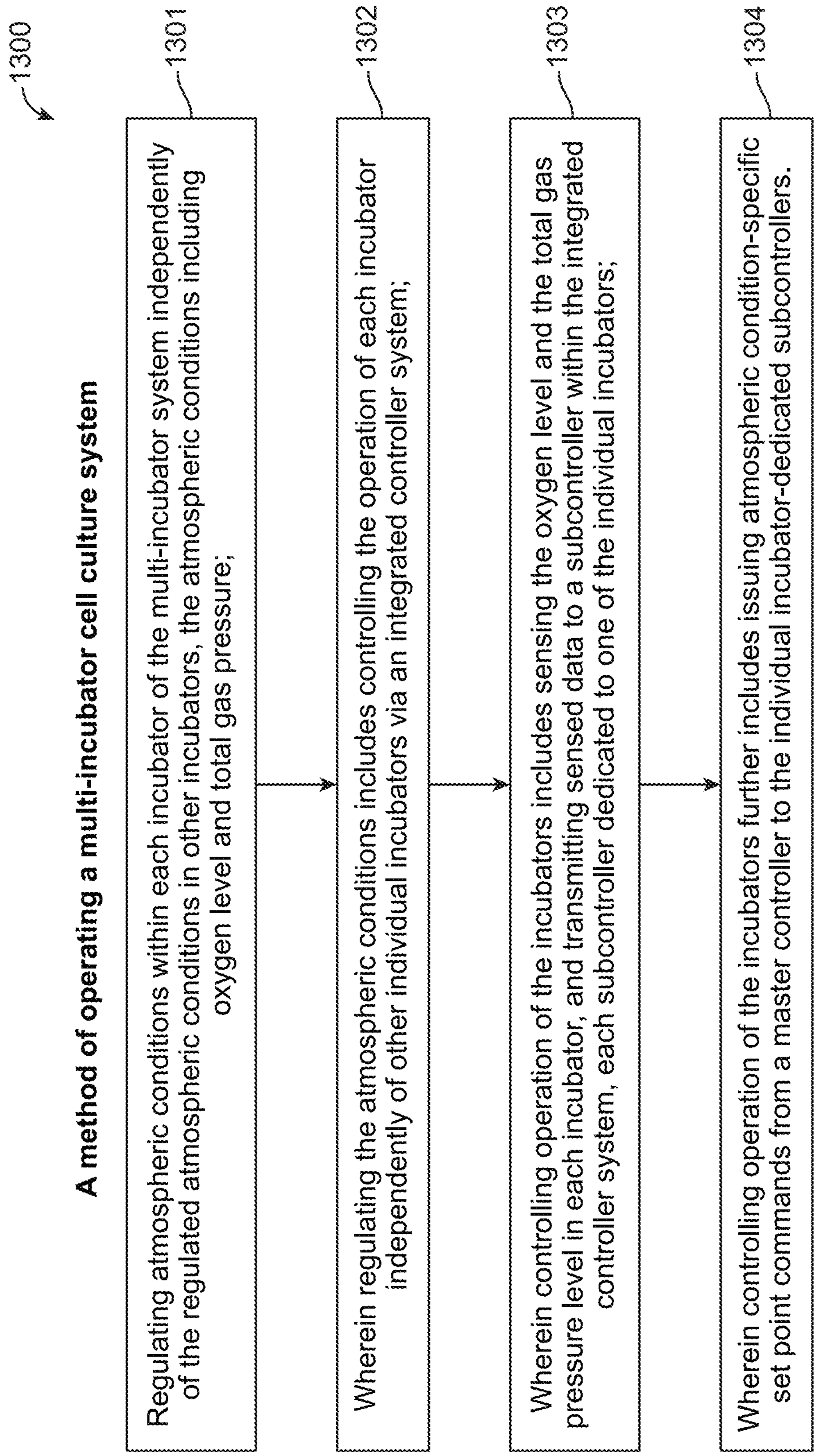
FIG. 13 is a flow diagram of a method of operating a multi-incubator cell culture system in which each individual incubator has independent atmospheric regulation.
Figure 14:
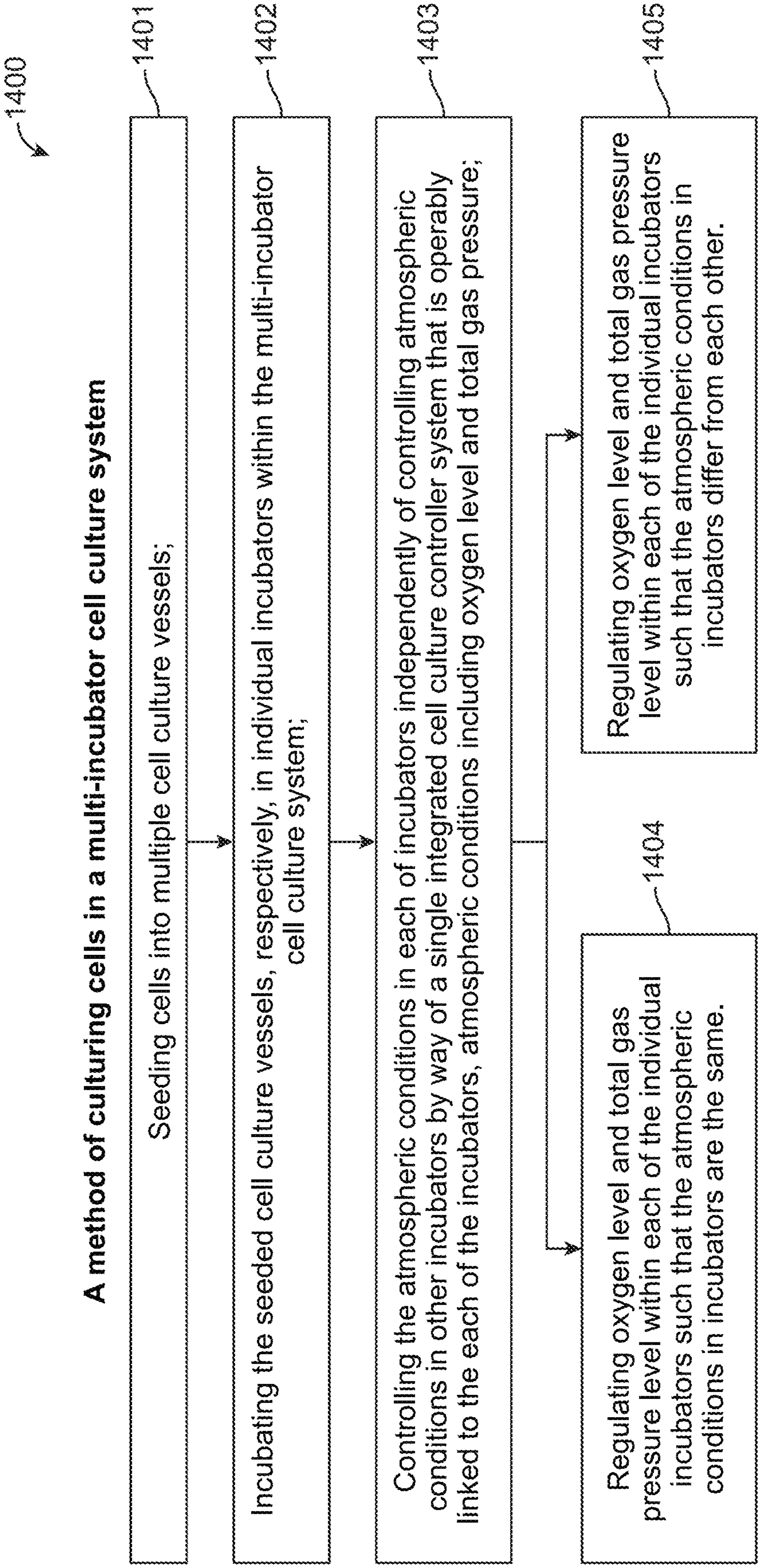
FIG. 14 is a flow diagram of a method of culturing cells in multi-incubator cell culture system in which each individual incubator has independent atmospheric regulation.

FIGS. 13-14 are flow diagrams of methods of operating multi-incubator cell culture system and culturing cells therein. Regarding methods of operating embodiments of multi-incubator cell culture system 10, as provided herein, in general, master controller 41 issues gas level set point commands to a subcontroller 42. Subcontroller 42, in turn, issues commands to modules in incubator 20 and receives sensory input from incubator 20. In response to received set point commands, incubator 21 regulates inflow and efflux of gases to bring the composition and pressure of gases within chamber 21 to be into compliance with set point commands originated by master controller 41.

FIG. 1 shows an embodiment of multi-incubator cell culture system 10, with a particular focus on single integrated controller system 40, which includes master controller 41 and multiple subcontrollers 42. Also shown are three individual incubators 20, each incubator has an environmental chamber 21. The use of three individual incubators is merely an example of "multiple" or "two or more" incubators. Each subcontroller 42 is dedicated to the control of a single incubator 20. In typical embodiments, each subcontroller 42 is included within or near the incubator 21 to which it is dedicated, but other than electrical connections, direct physical association between subcontroller and incubator is not necessary.

Master controller 41 is in direct operational communication with each subcontroller 42 and in typical embodiments, master controller 41 is configured to exert operational control of each of the individual incubators 20 by way of its dedicated subcontroller 42. However, in some embodiments, master controller 41 may be configured to exert direct control over an individual incubator 20. Arrows in FIG. 1 indicate directionality of controlling communications. In general, communications from master controller 41 to a subcontroller 42 relate to set point commands, and communications from a subcontroller to its respective incubator 20 relate to controlling gas influx or efflux from incubator chamber 21. And, as noted, in some instances, controlling communications can bypass subcontroller 41 and go directly to incubator 20.

Communication originating from master controller 41 that is directed to a subcontroller 42 typically includes commands regarding operation of an atmospheric regulation system in the form of atmospheric condition set points for each individual incubator 20. These set point commands are typically more directly implemented by dedicated subcontrollers 42, as described further detail elsewhere. Atmospheric conditions with particular set points include oxygen level, total gas pressure level, and carbon dioxide level, and may further include temperature and humidity level set points. Each of these atmospheric conditions are sensed by gas-specific sensors disposed within the environmental chamber 21.

Communications originating from incubators 20 typically include atmospheric condition data sensed from within environmental chamber 21. These sensed data are typically directed to the respective subcontroller 42, which can then transmit the data to master controller 41, as described in further detail elsewhere.

By this arrangement of a single integrated controller system 40, the atmospheric conditions of within each environmental chamber 21 of each one of the multiple incubators 20 can be regulated independently of the atmospheric conditions in the other of the multiple incubators 20. Further, as described elsewhere, within each incubator, oxygen level and total pressure can be regulated independently of each other.

FIG. 2 shows an embodiment of a multi-incubator cell culture system 10 with two individual incubators 20, each under the control of a single integrated controller system 40 (as shown in FIG. 1), with particular attention to a gas flow system 60. The use of two individual incubators is merely an example of "multiple" or "two or more" incubators. The gas flow system is represented by the flow of nitrogen from its source 72 into incubator chambers 21 of incubators 20, the flow of carbon dioxide from its source 71 into incubator chambers 21 of incubators 20, and the flow of air (as an oxygen source) from its sources 73 into incubators 21. Nitrogen source 72 and carbon dioxide source 71 are typically compressed gas cylinders that feed into all incubator chambers 21. Air source 73 is typically represented by an intake pump included in each incubator. Not shown in FIG. 2 are pressure release vent 74 and atmospheric recycle loop 65, which are shown in the more detailed FIG. 3.

Integrated controller system 40 includes master controller 41 and each of the subcontrollers 42. Each incubator 20 includes an environmental chamber 21 and a display 24. Each subcontroller is operationally connected components of an atmospheric regulation system (seen in detail in FIG. 3) and the display of the incubator 20 with which they are associated.

FIG. 3 shows an isolated single incubator 20 of a multi-incubator cell culture system 10 embodiment under the control of a single integrated controller system 40, with particular attention to an atmospheric regulation system 30 (captured by an overhead bracket). By focusing on single incubator 20 of a multi-incubator system, a more detailed representation of sensors and hardware in incubator chamber 21 and control modules within both master controller 41 and subcontroller 42 than that of FIG. 2.

Atmospheric regulation system 30 includes a master controller 41 and a subcontroller 42, these parts indicated by overlapping brackets across the top of the figure. Incubator 20 brackets subcontroller 42 and environmental chamber 21, which includes a number of hardware and sensing features that are in communication with sensing and analytic modules within subcontroller 42. Integrated controller system 40 brackets master controller 41 and subcontroller 42.

Master controller 41 includes atmospheric sensing-and-responding modules 51 and analytic or active modules 53 that communicate with partner modules within subcontroller 42 by way of communications port 56. Modules within subcontroller 42, in turn, communicate with an array sensors and valves within incubator 20, or more specifically, within chamber 21 of incubator 20.

Modules within subcontroller 42 include display module 50-D, oxygen module 50-O, carbon dioxide module 50-CO2, total gas pressure module 50-P, temperature module 50-T, and humidity module 50-H.

Modules within incubator 20 or within the confines of environmental chamber 21 include air intake valve 61, oxygen sensor 80-O2, carbon dioxide valve 62, carbon dioxide sensor 80-CO2, nitrogen intake valve 63, pressure sensor 80-P, vent valve 64, temperature sensor 80-T, incubator heater 67, dehumidifying cooler-heater 66, humidity sensor 80-H, and analytical unit sensors (optical sensor 82-O and impedance sensor 82-I).

Display module 50-D, oxygen module 50-O, carbon dioxide module 50-CO2, pressure module 50-P, temperature module 50-T, and heat module 50-H (all within subcontroller 42) are all in communication with a counterpart array of modules 51 within master controller 41, by way of communications portal 56.

Further shown in FIG. 3 are display 24 (in communication with subcontroller 42), atmospheric recirculation path 65 (exiting and entering from environmental chamber 21, air (and oxygen) source 73, carbon dioxide source 71, nitrogen source 72 (all gas sources entering environmental chamber 21), and gas vent 74 (exiting environmental chamber 21).

Air intake valve module 61 (of incubator 21) is in communication with oxygen module 50-O of subcontroller 42. Oxygen sensor module 80-O2 (of incubator 21) is also (in addition to air intake valve module 61) in communication with oxygen module 50-O of subcontroller 42. Accordingly, in response to an oxygen level lower than the oxygen set point, as reported by oxygen sensor module 80-O2, and in response to oxygen module 50-O2 of subcontroller 42, air intake valve 61 allows intake of air, as for example, by way of an air pump, which raises the oxygen level within the environmental chamber by virtue of the oxygen content of air.

Carbon dioxide valve module 62 (of incubator 21) is in communication with carbon dioxide module 50-CO2 of subcontroller 42. Carbon dioxide sensor module 80-CO2 (of incubator 21) is also in communication with carbon dioxide module 50-CO2 of subcontroller 42. Accordingly, in response to a carbon dioxide level lower than the carbon dioxide set point, as reported by carbon dioxide sensor module 80-CO2, and in response to carbon dioxide module 50-CO2, carbon dioxide valve module 62 releases carbon dioxide into environmental chamber 21, thereby increasing the carbon dioxide level to attain the carbon dioxide set point.

Nitrogen intake valve module 63 (of incubator 21) is in communication with pressure module 50-P of subcontroller 42. Nitrogen intake value 63 (of incubator 21) is also in communication with pressure module 50-P of subcontroller 42. Pressure sensor module 80-P (of incubator 21) is in communication with pressure module 50-P of subcontroller 42. Vent valve module 64 (of incubator 21) is in communication pressure module 50-P of subcontroller 42.

In response to a total gas pressure lower than the pressure set point, as reported by pressure module 80-P, nitrogen intake valve module 63 allows the intake of nitrogen into environmental chamber 21, thereby increasing pressure in the chamber to attain the pressure set point.

In response to an oxygen level greater than the oxygen set point, as reported by oxygen sensor 80-O2, nitrogen intake valve module 63 allows the intake of nitrogen into environmental chamber 21, thereby lowering the oxygen level, by dilution, to attain the oxygen set point.

Influx of nitrogen, in response either to a low oxygen level, may increase total gas pressure to a level above the pressure level set point. In response to a pressure greater than the pressure set point, as reported by pressure module 50-P, vent valve module 64 allows the escape of gas form environmental chamber 21 into the external environment, thereby allowing pressure to return to the pressure set point.

There is further description of the regulation of air, oxygen, nitrogen, and pressure in a section below under the heading of "method of operating a multi-incubator cell culture system".

Temperature sensor module 80-T (of incubator 21) is in communication with incubator temperature module 50-T of subcontroller 42. Incubator heater module 67 (of incubator 21) is in communication with and responsive to incubator temperature module 50-T of subcontroller 42. Accordingly, when the temperature within incubator 21 is below the temperature set point, incubator heater module 67 activates a heater in the incubator to bring temperature up to the temperature set point.

Typically, a cell culture incubator operates at the humidity dew point, but there may be occasions in which it is desirable to operate at a humidity level below dew point; thus, a dehumidifying cooler-heater unit may be disposed within incubator 21. Accordingly, humidity sensor module 80-H (of incubator 21) is in communication with humidity module 50-H of subcontroller 42. And dehumidifying cooler-heater module 66 (of incubator 21) is in communication with humidity module 50-H of subcontroller 42.

In general, as described above, master controller 41 directs controlling communication in the form of set point commands to subcontroller 42, which then implements commands by way of controlling influx of gases (air, oxygen, and carbon dioxide) into environmental chamber 21 of incubator 20. However, some embodiments of atmospheric regulation system 30 allow subcontroller 42 a degree of autonomy.

For example, embodiments of master controller 41 are typically configured such that when an atmospheric condition within an environmental chamber of one of the incubator chambers is sensed as being out of set point compliance, the master controller drives, by way of the gas flow system 60, a transition of the atmospheric condition (e.g., oxygen or carbon dioxide) within the environmental chamber 21 toward the set point of the gas, as mediated by the subcontroller 42 dedicated to the individual incubator 20.

However, in some embodiments of multi-incubator cell culture system 10, when an atmospheric condition within an environmental chamber 21 of an incubator 20 is sensed as being in-compliance with the atmospheric condition set point, the subcontroller 41 dedicated to the incubator is operable to control the gas flow system without an ongoing atmospheric set point command from the master controller.

Figure 12:
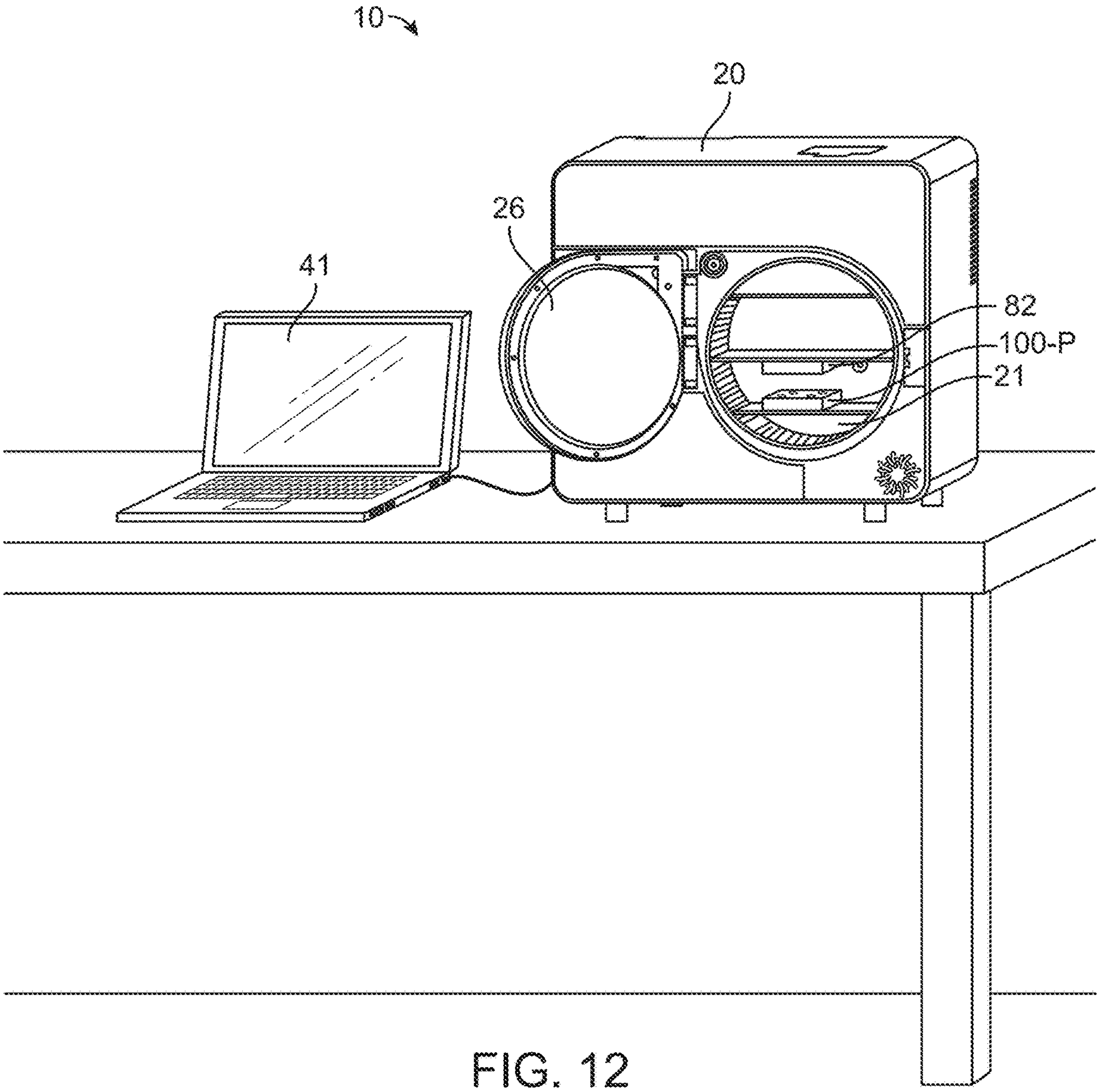
FIG. 12 shows a single incubator of a multi-incubator cell culture system with the incubator door open, allowing a view of a chamber that is hosting a cell plate and an analytical/function unit above it.

Some embodiments of incubators 20 within multi-incubator cell culture system 10 may include analytical or functional adjunct units, such as an optical sensor, an impedance sensor, or a current delivery unit 82 (as shown in FIG. 12). Thus, optical sensor module 82-O and impedance sensor module 82-I (of incubator 21) and a current delivery module (not shown) are in communication with analytics module 53 of master controller 41.

In general, as described above, master controller 41 directs controlling communication in the form of set point commands to subcontroller 42, which then implements commands by way of controlling influx of gases (air, oxygen, and carbon dioxide) into environmental chamber 21 of incubator 20. However, some embodiments of atmospheric regulation system 30 allow subcontroller 42 a degree of autonomy.

For example, embodiments of master controller 41 are typically configured such that when an atmospheric condition within an environmental chamber of one of the incubator chambers is sensed as being out of set point compliance, the master controller drives, by way of the gas flow system 60, a transition of the atmospheric condition (e.g., oxygen or carbon dioxide) within the environmental chamber 21 toward the set point of the gas, as mediated by the subcontroller 42 dedicated to the individual incubator 20.

However, in some embodiments of multi-incubator cell culture system 10, when an atmospheric condition within an environmental chamber 21 of an incubator 20 is sensed as being in-compliance with the atmospheric condition set point, the subcontroller 41 dedicated to the incubator is operable to control the gas flow system without an ongoing atmospheric set point command from the master controller.

Figure 4:
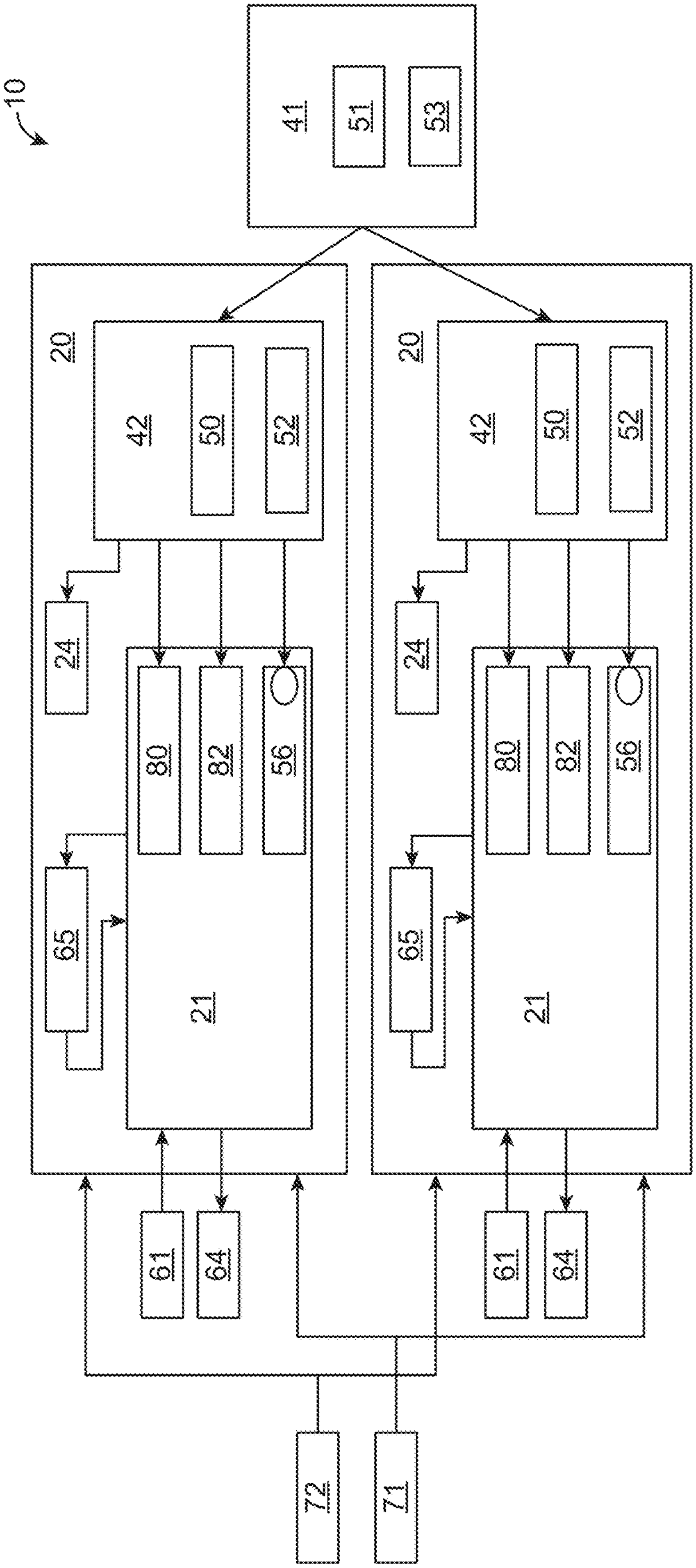
FIG. 4 shows a multi-incubator cell culture system embodiment under the control of a single integrated controller system, further showing aspects of a gas flow system.

FIG. 4 shows an embodiment of a multi-incubator cell culture system 10 under the control of a single integrated controller system, further showing aspects of a gas flow system. FIG. 4 is consistent with FIGS. 1-3; it has more detail than FIG. 2, and less detail than FIG. 3. FIG. 4 focuses on the distribution and independence of the operational control of the two exemplary incubators 20 by way of an integrated control system represented by a single master controller 41 and the two subcontrollers 42, each subcontroller dedicated, respectively, the one of the two incubators 20.

Master controller 41 has a set of control modules 51 dedicated to control of atmospheric gases within the environmental chambers 21 of incubators 20. Control modules 51 exert control primarily by way of transmitting atmospheric gas and pressure set points to subcontrollers 42. Control modules 51 are configured to allow independent operation of incubators 20 with respect to gas composition. Accordingly, incubators 20 are independently operable. The atmospheric gas and pressure set points transmitted to atmospheric condition modules 50 of incubators 20 be identical (in which case incubators 20 operate in parallel) or they may be different (in which case incubators 20 operate in a non-parallel manner).

Atmospheric sensors (gases and pressure) 80 within or in communication environmental chambers 21 are in communication with master controllers 42. Master controllers 42 are in control of the operation of air injection valves 61, pressure release vents 64, nitrogen intake from source 72, carbon dioxide intake from source 71, and operation of gas recirculation path 65 of each individual incubator 20.

FIGS. 5-12 show various configurations of a multi-incubator cell culture system 10. FIGS. 5-8 show variations of the system with different numbers of individual incubators 20. FIGS. 9-12 show internal views of a single representative incubator 20 with incubator chamber door 26 open, and a variety of cell culture vessels disposed therein. In all embodiments, a single master controller 41, in the form of a laptop computer is controlling the operation of all incubators 20 within the multi-incubator cell culture system 10.

Figure 5:
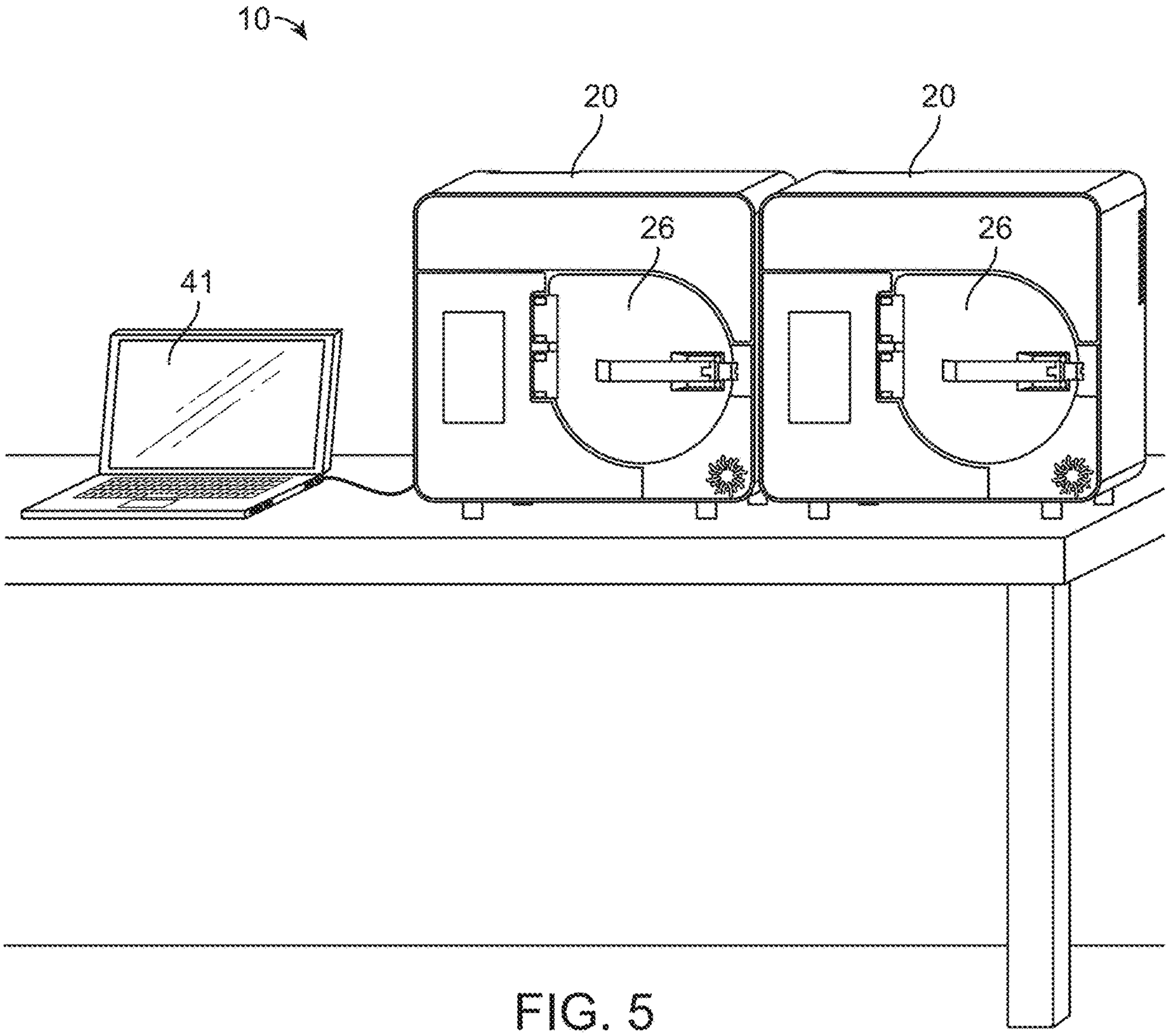
FIG. 5 shows a two-incubator embodiment a multi-incubator cell culture system, each incubator being free-standing.
Figure 6:
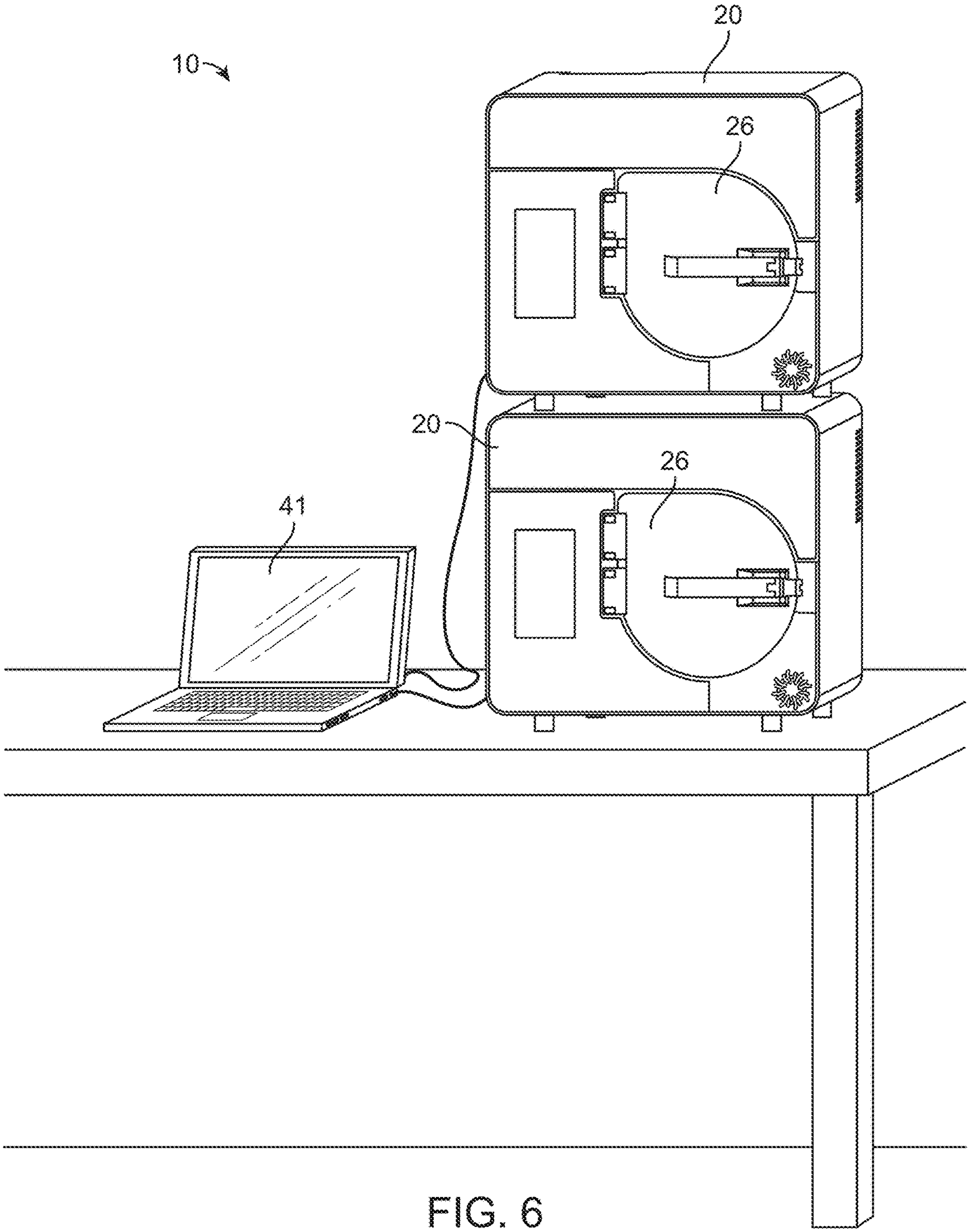
FIG. 6 shows a two-incubator embodiment a multi-incubator cell culture system, one incubator being stacked on top of the other.
Figure 7:
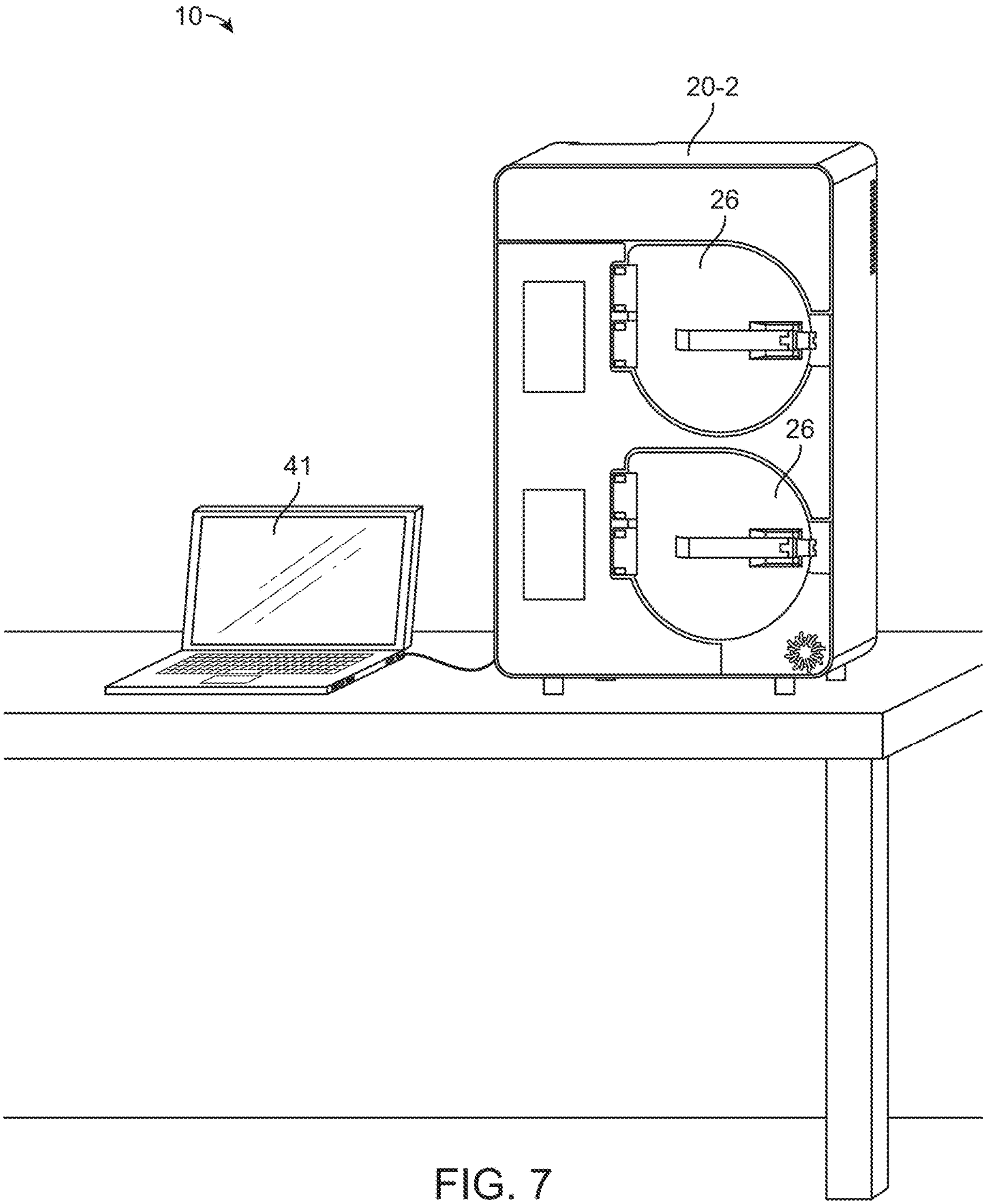
FIG. 7 shows a two-incubator embodiment a multi-incubator cell culture system, the two incubators a multi-incubator cell culture system being arranged within a single housing.
Figure 8:
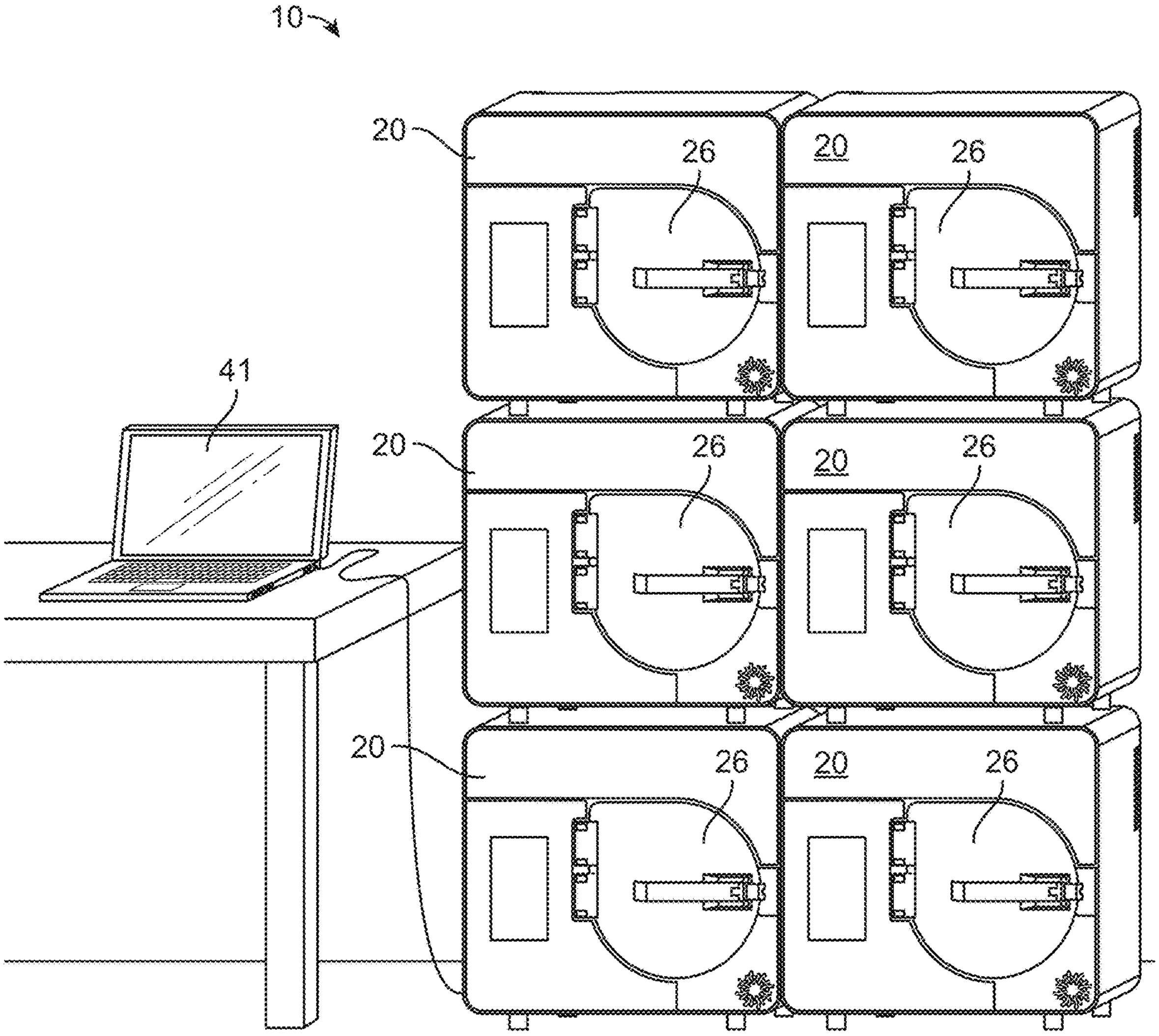
FIG. 8 shows a six-incubator embodiment a multi-incubator cell culture system, the six individual incubators arranged as two side-by-side stacks of three incubators.

FIG. 5 shows a two-incubator embodiment a multi-incubator cell culture system 10 and a single computer serving as a master controller 41, each incubator being free-standing. FIG. 6 shows a two-incubator embodiment a multi-incubator cell culture system 10 and a single computer serving as a master controller 41, the two incubators being stacked one over the other. FIG. 7 shows a two-incubator embodiment a multi-incubator cell culture system 10 and a single computer serving as a master controller 41, the two incubators a multi-incubator cell culture system being arranged within a single housing. FIG. 8 shows a six-incubator embodiment a multi-incubator cell culture system 10 and a single computer serving as a master controller 41, the six individual incubators arranged as two side-by-side stacks of three incubators.

The internal volume of an environmental chamber 21 of an incubator 20 (of a multi-incubator cell culture system 10) is sufficient to accommodate a number of types of conventional cell culture vessels. In one particular example, environmental chamber 21 encompasses a volume of about 4.5 cubic feet, but chamber volumes may be larger or smaller than 4.5 cubic feet. FIGS. 9-12 are conceptual depictions, not intended to reflect scale or proportion. Further aspects of dimensionality and applications of incubators 20 are described after the following descriptions FIGS. 9-12.

Figure 9:
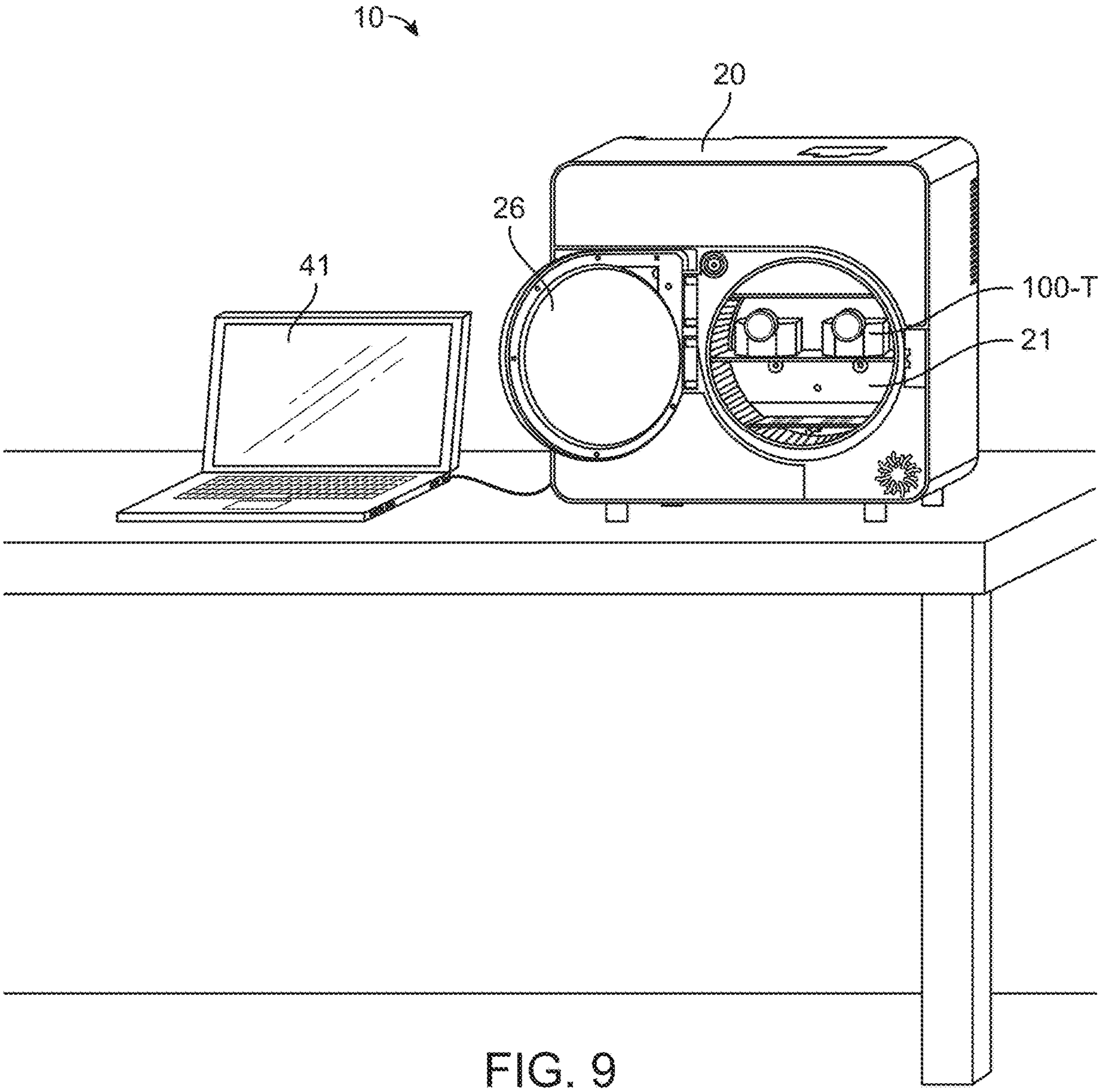
FIG. 9 shows a single incubator of a multi-incubator cell culture system with the incubator door open, allowing a view of a chamber with a shelf that accommodates cell culture T-flasks.
Figure 10:
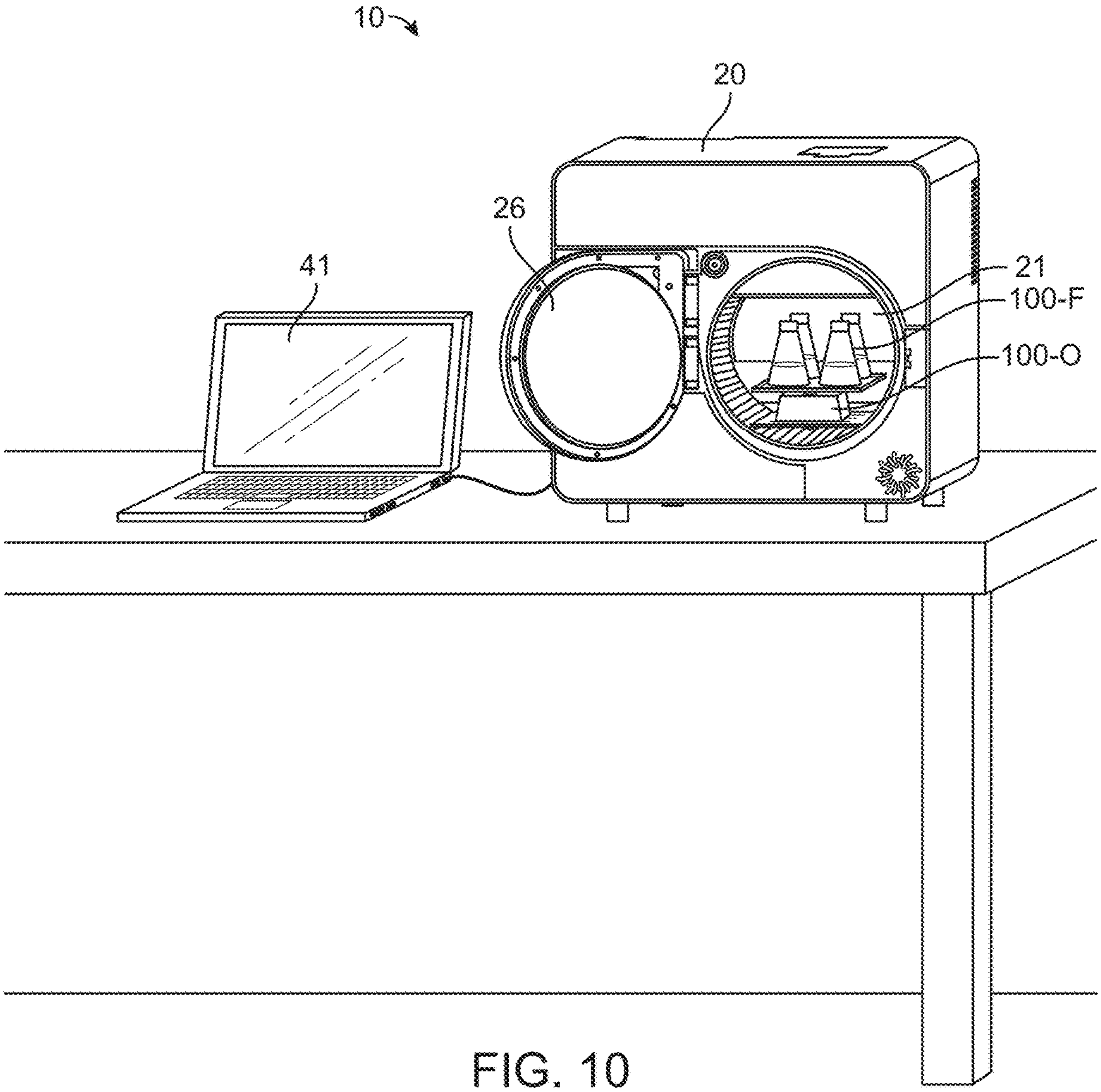
FIG. 10 shows a single incubator of a multi-incubator system cell culture system with the incubator door open, allowing a view a chamber that is hosting a cell culture shake flask positioned on an orbital shaker.
Figure 11:
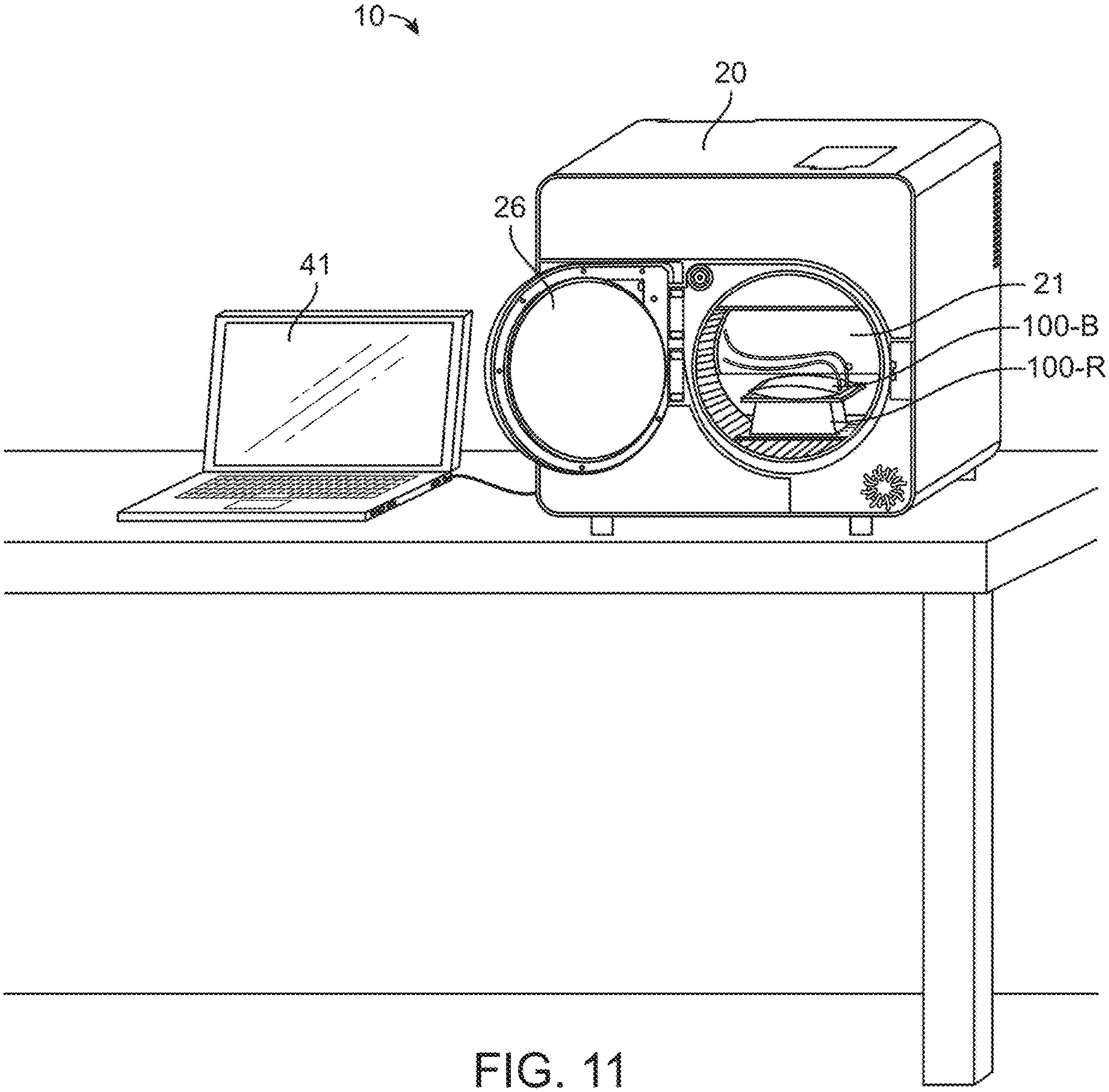
FIG. 11 shows a single incubator of a multi-incubator cell culture system with the incubator door open, allowing a view of a chamber that is hosting a cell culture bag positioned on a rocking platform.

FIG. 9 shows a single incubator 20 of a multi-incubator cell culture system 10 with the incubator door 26 open, allowing a view of chamber 21 with a shelf that accommodates cell culture T-flasks 100-T. FIG. 10 shows a single incubator 20 of a multi-incubator cell culture system 10 with the incubator door 26 open, allowing a view chamber 21 that is hosting cell culture shake flasks 100-F positioned on an orbital shaker 100-O. FIG. 11 shows a single incubator 20 of a multi-incubator cell culture system 10 with the incubator door 26 open, allowing a view of chamber 21 that is hosting a cell culture bag 100-B positioned on a rocking platform 100-R. FIG. 12 shows a single incubator of a multi-incubator cell culture system with the incubator door open, allowing a view of a chamber that is hosting a cell culture plate 100-P and an analytical/functional unit 82 positioned above it. An analytical/functional unit may be any of an optical sensor, impedance sensor, or a current delivery unit.

In one embodiment of the technology, a cell culture incubator 20 (within a multi-incubator cell culture system 10) is sized and configured to accommodate a scaled cell culture vessel that is supported by a vessel agitator. Accordingly, a cell culture incubator embodiment, as provided herein, includes an enclosed environmental chamber and an integrated controller system operably communicative with the enclosed environmental chamber. The integrated controller system is configured to regulate an oxygen level and a total gas pressure within the enclosed environmental chamber, wherein the oxygen level and the total gas pressure are regulated independently of each other. The enclosed environmental chamber is sized and configured to accommodate a cell vessel supported by an agitating device, the agitating device is able to provide sufficient agitation that a cell culture medium within the vessel is well mixed with regard to gases dissolved in the cell culture medium, and, if cells being cultured are in suspension, the agitation mechanism further serves to maintain a substantially homogeneous distribution of cells in the cell culture medium.

Some embodiments of a cell culture incubator 20 further include an aseptic fluid flow system that communicates between an external source of cells in suspension and a cell culture vessel disposed within the cell culture incubator. In some embodiments, the aseptic fluid flow system further communicates between the cell culture vessel and a sample holding vessel external to the cell culture vessel.

In some embodiments of a cell culture incubator 20, the accommodated cell culture agitating device (for which the incubator is sized and configured) may be of any conventional design, such as a rocking platform, an orbiting platform, or a magnetic stirring driver. In typical embodiments, the accommodated cell culture vessel accommodates a liquid cell culture medium of at least 100 ml.

Some embodiments of a cell culture incubator 20 include a robotic system configured to make aseptic fluid flow connections (A) between an external source of cell culture medium and a cell culture vessel positioned within the incubator, and (B) between cell culture medium within the cell culture vessel and a cell culture sample receptacle external to the cell culture vessel. In some of these embodiments, the cell culture sample receptacle external to the cell culture vessel is also external to the enclosed environmental chamber.

Various methods by which a cell culture incubator 20, one sized and configured to accommodate a cell culture vessel supported by an agitating device (as described above) can be operated. A method of monitoring a cellular presence on a surface of a cell culture vessel includes culturing cells in a liquid culture medium, the medium being contained within a cell culture vessel, and the vessel being disposed within a culture incubator. The method further includes receiving both impedance data informative of impedance to electrical current flow between mapping electrodes disposed within the cell culture surface and receiving optical data transmitted from the optical mapping grid within the cell culture surface. The method further includes both processing the impedance data into an electrical measure of cellular presence; and processing the optical data into an optical measure of cellular presence.

In one embodiment of the technology, a cell culture incubator 20 is included within a larger multi-incubator cell culture system; that system includes an incubator scaled as in the fifth embodiment, as well as a scaled cell culture vessel and an agitating device. Accordingly, a cell culture incubator, a cell culture vessel that has a liquid holding volume greater than about 100 ml; and an agitation mechanism able to provide sufficient agitation that a cell culture medium within the cell culture vessel is mixed to a state of substantial homogeneity with regard to gases dissolved in the cell culture medium. The cell culture incubator includes an enclosed environmental chamber and an integrated controller system operably communicative with the enclosed environmental chamber. The enclosed environmental chamber is sized and configured to accommodate a cell vessel supported by an agitating device. The integrated controller system configured to regulate an oxygen level and a total gas pressure within the enclosed environmental chamber; the oxygen level and the total gas pressure are regulated independently of each other.

In some embodiments of a cell culture incubator system 10, the integrated controller system includes a cell agitation device control module configured to control a rate of agitation and agitation on-off control.

In some embodiments of a cell culture incubator system 10, the cell culture vessel is a cell culture bag (see FIG. 11), such as may be used during an immunotherapy work flow. In some of these embodiments, cell culture bag includes a sampling port, through which a cell culture sample volume can be drawn aseptically.

In some embodiments of a cell culture incubator system 10, the cell culture incubator includes a fluid handling system configured to make aseptic fluid flow connections (A) between an external source of cell culture medium and a cell culture vessel positioned within the incubator, and (B) between cell culture medium within the cell culture vessel and a cell culture sample or harvest receptacle external to the cell culture vessel.

In some embodiments of a cell culture incubator system 10, the fluid handling system includes a robotic connecting mechanism configured to make fluid flow connections within the environmental chamber while the chamber remains closed. In particular examples of these embodiments, the external source of cell culture medium comprises an apheresis system such that a fluid stream containing a cell population derived from the apheresis system can enter the incubator in an aseptic manner.

Embodiments of the provided technology include various methods by which a cell culture incubator system 10 that includes an incubator 20 that includes a cell culture vessel and a vessel agitating device (as described above) can be operated. A method of culturing cells in a cell culture incubator includes aseptically transferring a first volume of cell culture medium containing a cell population from a reservoir external to the cell culture incubator into the cell culture vessel disposed within the cell culture incubator, to establish a seed cell population, and then culturing the seed cell population within the cell culture vessel for a culture duration to allow growth of the seed population to an expanded cell population. The method further includes aseptically transferring a second volume of cell culture medium containing the expanded cell population from the cell culture vessel into a cell sampling or cell harvesting container. In particular examples of these embodiments, each of the aseptic fluid transferring steps includes making the fluid transfer connection robotically so that it is not necessary to open a door of the chamber and make fluid connections manually.

In one embodiment of the technology, a multi-incubator cell culture system is provided. Each component incubator unit includes an enclosed environmental chamber and an integrated controller system operably communicative with the enclosed environmental chamber. The controller system is configured to regulate an oxygen level and a total gas pressure within the enclosed environmental chamber; the oxygen level and the total gas pressure are regulated independently of each other. Each of the multiple incubator units includes one or more of the following features: (a) an impedance mapping module configured to receive grid site-tagged impedance data transmitted from an electrode mapping grid included within a cell culture surface of a cell culture vessel housed within the cell culture incubator, and wherein the mapped impedance data are processable into a map of cellular attachment to the cell culture surface of the cell culture vessel, (b) an optical mapping module configured to receive optical mapping grid site-tagged optical data transmitted from an optical mapping grid the optical mapping grid included within a cell culture surface of a cell culture vessel housed within the cell culture incubator, and wherein the mapped optical data are processable into a map of cellular presence on the cell culture surface of the cell culture vessel, (c) a current delivery module configured to transmit electrical current by way of an electrode array disposed within a cell culture surface of a cell culture vessel housed within the cell culture incubator, the transmitted current being effective to electroporate a cell adhering to the cell culture surface, or (d) a size and configuration sufficient to accommodate one or more cell culture vessels, each with a capacity of at least 100 ml, and a supportive cell culture vessel agitation mechanism.

Some embodiments of the multi-incubator cell culture system further include an integrated controller system configured to control each of the multiple component incubators. Some embodiments of the multi-incubator cell culture system further include an integrated controller system configured to control all individual cell culture units such that the individual cell culture units can be operated in parallel with regard to oxygen level and total gas pressure within the individual incubator units. In some embodiments, an integrated controller system is configured to control all individual cell culture units such that the individual cell culture units can each be operated independently with regard to oxygen level and total gas pressure within the individual incubator units.

In some embodiments of the multi-incubator cell culture system, the individual incubator units are configured to be stackable. Some of these embodiments are particularly configured for side-by-side close compatibility. One embodiment of the multi-unit cell culture incubator system includes a set of between two and six individual incubator units. A particular embodiment consists of a set of six individual incubators, the set of six individual incubators arranged as two units side-by-side, in side-by-side stacks of three units.

Various methods by which a multi-incubator cell culture system (that includes several separate incubator units, as described above) can be operated. One particular method of culturing cells in a multi-unit cell culture incubator system includes regulating an oxygen level and a total gas pressure level within all of the component incubator units in a parallel manner such that an oxygen level value and a total gas pressure level value in each of the component incubator units are substantially identical over a cell culture duration or workflow.

Atmospheric Regulation System

Some embodiments of a cell culture incubator 20 (as described herein in the context of a multiple-incubator system 10) include an atmospheric regulation system 30 that is applicable to the collective individual incubators 20 of a multi-incubator cell culture system 10. Embodiments of multiple-incubator system 10 and aspects of atmospheric regulation system 30 are shown in FIGS. 1-4. For simplicity in describing these embodiments atmospheric regulation system 30, an individual cell culture incubator 20 may be referred to in the singular with the intention of describing but one incubator among the multiple incubators 20 within a multiple-incubator system.

Embodiments of the atmospheric regulation system 30 have an integrated controller system 40 that is operably linked to the environmental chamber 21. The integrated controller system includes an oxygen module 50-O and a pressure module 50-P. The atmospheric regulation system further includes an oxygen sensor 80-O configured to measure the oxygen level within the environmental chamber 21 and to convey an oxygen level signal to the oxygen module 50-O, a pressure sensor 80-P configured to measure the total gas pressure within the environmental chamber and to convey an pressure level signal to the pressure module 50-P, and a gas flow system 60 having multiple gas sources flowably connected to the environmental chamber. The gas sources include a nitrogen source, a carbon dioxide source, and an air source, wherein gas flow from each source is regulated by the integrated controller system.

Embodiments of an integrated controller system 40 are configured to regulate each of an oxygen level and a total gas pressure within the environmental chamber 21, and the controller system is configured to: (a) provide a hypoxic oxygen set point to the oxygen module 50-O, and (b) provide a hyperbaric total gas pressure set point to the pressure module 50-P. The regulation of the oxygen level to the hypoxic set point prevails despite an oxygen partial pressure-increasing effect of the hyperbaric pressure condition, per the positive pressure set point.

In some embodiments of atmospheric regulation system 30 (of a multi-incubator cell culture system 10), in addition to oxygen module 50-O and a pressure module 50-P, integrated controller system 40 further includes one or more of a carbon dioxide module 50-CO, a temperature module 50-T, or a humidity module 50-H; these modules are informed, respectively, by a carbon dioxide sensor 80-CO2, a temperature sensor 50-T, or a humidity sensor 50-H, these sensors being disposed within the environmental chamber 21 of cell culture incubator 20. Still further modules may be included within the integrated controller system 40, such as analytical modules, as described elsewhere herein.

In some embodiments of atmospheric regulation system 30, the gas flow system 60 further includes: gas flow pathways for gases, the gases including any one or more of carbon dioxide, nitrogen, or air, these gas pathways including for each gas, respectively, any one or more of a gas line 66, a valve, an inlet, or a vent, such as a controlled vent 74.

In some embodiments of atmospheric regulation system 30, the regulated nitrogen flow is directed into the environmental chamber 21 by way of a chamber gas flow path, and the regulated nitrogen flow includes a response to oxygen sensor data via the oxygen module 50-O. In the response to a sensed oxygen level that is above the oxygen set point, the response may include a command to flow nitrogen into the environmental chamber 21. The effect of flowing nitrogen into a chamber 21 with oxygen at a level above set point, when coupled with release of internal atmospheric gas from vent 64, is to lower the oxygen level by dilution.

In some embodiments of atmospheric regulation system 30, the regulated nitrogen flow is directed into the environmental chamber 21 by way of a chamber gas flow path, and the regulated nitrogen flow includes a response to carbon dioxide sensor data via the carbon dioxide module 50-CO2. In the response to a sensed carbon dioxide level that is above the carbon dioxide set point, the response may include a command to flow nitrogen into the environmental chamber 21.

The effect of flowing nitrogen into a chamber 21 with carbon dioxide at a level above set point, when coupled with release of internal atmospheric gas from vent 64, is to lower the carbon dioxide level by dilution.

In some embodiments of atmospheric regulation system 30, the regulated nitrogen flow is directed into the environmental chamber 21 by way of a chamber gas flow path. The regulated nitrogen flow includes a response to pressure sensor data by way of the pressure module 50-P. The response to a pressure level that is below the pressure set point includes a command to flow nitrogen into the environmental chamber 21. In some of these embodiments, as a result of an increase in pressure level within the environmental chamber 21 by the flow of nitrogen, the pressure level reaches the pressure set point, and the integrated controller system 40 then commands a cessation of the nitrogen flow into the environmental chamber.

In some embodiments of atmospheric regulation system 30 (of multi-incubator cell culture system 10), the regulation of pressure within environmental chamber 21 by integrated controller system 40 includes a response (or responses) to pressure sensor 80-P, as mediated by the pressure module 50-P, when a sensed pressure is out of compliance with a pressure set point. In response to a pressure level lower than the pressure set point, some embodiments of the atmospheric regulation system 30 are configured to respond by initiating an inflow of nitrogen.

In response to a pressure level higher than the pressure set point, some embodiments of atmospheric regulation system 30 are configured to respond to a pressure higher than the pressure set point by initiating a controlled efflux or outflow of gas from the environmental chamber 21 by way of a vent 74.

In typical embodiments of atmospheric regulation system 30, the regulation of carbon dioxide flow into the environmental chamber 21 by integrated controller system 40 includes a response to a carbon dioxide sensor 80-P configured to measure the carbon dioxide level within the environmental chamber. When the level of carbon dioxide is below the carbon dioxide set point, the system is configured to initiate an inflow of carbon dioxide. In a complementary manner, when the level of carbon dioxide is above the carbon dioxide set point, the system is configured to cease inflow of carbon dioxide. And, as noted above, in the response to a sensed carbon dioxide level that is above the carbon dioxide set point, the response may include a command to flow nitrogen into the environmental chamber 21.

In particular embodiments of atmospheric regulation system 30, the oxygen level (typically a hypoxic level) within the environmental chamber 21 is regulated by oxygen module 50-O, and, in the event of sensing an oxygen level in the environmental chamber above the oxygen set point, the atmospheric regulation system commands the gas flow regulation system to regulate flow of a non-oxygen gas to dilute the level of oxygen to a particular setpoint. In these embodiments, the non-oxygen gas typically includes nitrogen. In general, the gas-regulation challenge faced by the atmospheric regulation system is to lower an oxygen level below an ambient level; typically, this accomplished by dilution, as noted, which is also typically accompanied by venting of internal atmospheric gas from environmental chamber 21 to maintain a specified total gas pressure.

Embodiments of atmospheric regulation system 30 may command the gas flow regulation system to an oxygen set point having a value within a range of about 0.10% to about 21% oxygen. In some of these embodiments, the atmospheric regulation system may command the gas flow regulation system to an oxygen set point having a value within a range of about 1% to about 12% oxygen. And in particular embodiments, the atmospheric regulation system may command the gas flow regulation system to an oxygen set point having a value within a range of about 2% to about 6% oxygen.

In some embodiments of atmospheric regulation system 30, the pressure level within the environmental chamber 21 is regulated by pressure module 50-P, and, in response to a pressure that is less than the pressure set point (which is typically above the ambient pressure), the atmospheric regulation system is configured to direct an inflow of nitrogen into the environmental chamber.

In some embodiments of atmospheric regulation system 30, the atmospheric pressure set point is within a range of about 0.5 PSIG to about 15 PSIG. In particular embodiments of the atmospheric regulation system, the pressure set point is within a range of about 1.0 PSIG to about 10 PSIG. In other embodiments of the atmospheric regulation system, the pressure set point is within a range of about 2.0 PSIG to about 7.5 PSIG. And in still further embodiments of the atmospheric regulation system, the pressure set point is within a range of about 2.5 PSIG to about 6.0 PSIG.

Method of Operating a Multi-Incubator Cell Culture System

FIG. 1 provides a representation of a method of controlling multiple incubators 20 by way of issuing atmospheric parameter set point commands from a master controller 41 to multiple subcontrollers 42 (each subcontroller dedicated to one of the multiple incubators), and then issuing operational commands from each subcontroller 42 to its dedicated incubator 20. FIG. 2 elaborates further, showing that as a consequence of commands being issued from each subcontroller 42, elements of a gas regulation system 60 are regulating atmospheric parameters within the environmental chamber 21 of each incubator 20 (including, in particular the oxygen level and the total gas pressure). FIG. 3 elaborates still further, showing that regulating atmospheric parameters within the environmental chambers 21 includes sending data from atmospheric parameter sensors back to subcontrollers 42, such data acting as feedback regulation to facilitate compliance with set point commands issued by master controller 41.

FIG. 13 is a flow diagram of an exemplary embodiment of a method 1300 of operating a multi-incubator cell culture system in which each individual incubator has atmospheric regulation that is independent of other incubators. Method embodiment 1300 includes the action 1301 of regulating atmospheric conditions within each incubator in the multi-incubator system independently of the regulated atmospheric conditions in other incubators, the atmospheric conditions including oxygen level and total gas pressure. Regulating the atmospheric conditions includes controlling the operation 1302 of each incubator independently of other individual incubators via an integrated controller system. Controlling operation of the incubators includes actions 1303 of sensing the oxygen level and the total gas pressure level in each incubator, and transmitting the sensed oxygen and pressure data to a subcontroller within the integrated controller system, each subcontroller being dedicated to one of the individual incubators. Controlling operation of the incubators further includes action 1304 of issuing atmospheric condition-specific set point commands from a master controller to the individual incubator-dedicated subcontrollers.

A more detailed rendering of embodiments of operating a multi-incubator cell culture system will now be provided. Embodiments of the technology disclosed herein include methods of operating individual cell culture incubators 20 within multi-incubator cell culture system 10, as described herein, and as shown in FIGS. 1-4. In one embodiment, a method of operating such a cell culture system 10 includes regulating atmospheric conditions within each individual incubator 20 independently of the regulated atmospheric conditions in the one or more other individual incubators. Those regulated atmospheric conditions include, in particular, oxygen level and total gas pressure. Further, implementation of method of operating embodiments, regulating the atmospheric conditions in the two or more individual incubators 20 is under the control of a single integrated controller system 40, the controller system being configured to control operation of each individual incubator independently of the one or more other individual incubators.

In some embodiments of a method of operating multi-incubator cell culture system 10, regulating the atmospheric condition setpoints includes sensing the oxygen level and the total gas pressure level in each of the environmental chambers 21 of the individual incubators 20, and transmitting the sensed data to a subcontroller 42 within the integrated controller system 40, each subcontroller dedicated to one of the two or more individual incubators.

In particular embodiments of a method of operating a multi-incubator cell culture system 10, regulating atmospheric conditions includes issuing one or more atmospheric condition set point commands from master controller 41 to an individual incubator-dedicated subcontroller 42 within integrated controller system 40.

In particular embodiments of a method of operating multi-incubator cell culture system 10, the atmospheric condition set points include a set point for the oxygen level and a set point for the total gas pressure level.

In particular embodiments of a method of operating multi-incubator cell culture system 10, issuing one or more atmospheric set point commands is done in accordance with an operator input into single integrated controller system 40. In alternative embodiments, issuing one or more atmospheric set point commands may be done in accordance with a preset cell culture workflow program.

In particular embodiments of a method of operating multi-incubator cell culture system 10, issuing one or more atmospheric set point commands occurs during an instance when at least one of the current atmospheric conditions is out of compliance with the respective set point level. And on the other hand, in particular embodiments of operating a multi-incubator cell culture system 10, issuing one or more commands regarding atmospheric set points includes a command to maintain atmospheric conditions that are already in accordance with the atmospheric set points.

In some embodiments of a method of operating multi-incubator cell culture system 10, regulating atmospheric conditions comprises adhering to rules governing a gas flow regulation system in accordance with atmospheric set points, these set points including an oxygen level set point, a carbon dioxide set point, and a total gas pressure set point, these rules being implemented by the integrated system controller system.

In one embodiment, a rule governing the oxygen level includes flowing air into the environmental chamber 21 in response to an oxygen level being sensed as below the oxygen set point. The rationale for this rule is that air includes oxygen, therefore an influx of oxygen results in an increase in oxygen level.

In one embodiment, a rule governing the carbon dioxide level includes flowing carbon dioxide into the environmental chamber in response to a carbon dioxide level being sensed as below the carbon dioxide set point. The rationale for this rule is that air has a very low level of carbon dioxide, therefor an influx of air results in a decrease in carbon dioxide level.

In some embodiments, rules governing nitrogen flow into the environmental chamber 21 include flowing nitrogen in response to any one or more of (a) the total gas pressure being sensed as below the pressure set point, (b) the oxygen level being sensed as above the oxygen set point, or (c) the carbon dioxide being sensed as above the carbon dioxide set point. The rationale for these rules are, respectively, (a) an influx of nitrogen increases the total pressure without complicating the levels or partial pressures of oxygen or carbon dioxide, (b) an influx of nitrogen reduces the level of oxygen by dilution, and (c) an influx of nitrogen reduces the level of carbon dioxide by dilution.

Method of Culturing Cells in a Multi-Incubator System

FIG. 14 is a flow diagram of an embodiment of a method 1400 of culturing cells in multi-incubator cell culture system in which each individual incubator has independent atmospheric regulation. Method embodiment 1400 includes the action 1401 of seeding cells into multiple cell culture vessels. Method embodiment 1400 further includes the action 1402 of incubating the seeded cell culture vessels, respectively, in individual incubators within the multi-incubator cell culture system. Method embodiment 1400 further includes the action 1403 of controlling the atmospheric conditions in each of incubators independently of controlling atmospheric conditions in other incubators by way of a single integrated cell culture controller system that is operably linked to the each of the incubators, atmospheric conditions including oxygen level and total gas pressure.

At least two actions may follow action 1403. In one exemplary action 1404, regulating oxygen level and total gas pressure level within each of the individual incubators occurs such that the atmospheric conditions in incubators are the same. In an alternative exemplary action 1404, regulating oxygen level and total gas pressure level within each of the individual incubators such that the atmospheric conditions in incubators differ from each other 1405.

A more detailed rendering of embodiments of culturing cells in a multi-incubator cell culture system will now be provided. Embodiments of the technology disclosed herein include methods of culturing cells within individual incubators 20 of a multi-incubator cell culture system 10, as described herein, and as shown in FIGS. 1-4. Cell populations being cultured in the individual incubators within a workflow may be derived variously from a common seeding source or from different seeding sources. First, methods particularly relevant to culturing cells from a common seeding source will be described.

A method of culturing a cell population from a common seeding source within two or more individual incubators of a cell culture incubator system includes seeding cells from the common seeding source into two or more individual cell culture vessels, incubating the two or more seeded cell culture vessels, respectively, in the two or more individual incubators 20, and controlling the atmospheric conditions in each of the individual incubators independently by way of single integrated cell culture controller system 40 that is operably linked to the each of the individual incubators. Notably, each individual incubator herein 20 is capable of controlling internal atmospheric conditions independently of the internal atmospheric conditions in the other one or more incubators.

In some embodiments of multi-incubator cell culture system 10, each individual incubator 20 is configured to regulate atmospheric conditions, including, in particular, that oxygen level and the total gas pressure within the respective environmental chamber 21, the oxygen level and the total gas pressure being regulated independently of each other.

In some embodiments of a method of controlling the atmospheric conditions of two or more multiple incubators 20 within multi-incubator cell culture system 10, the method includes operating each of the incubators independently of the one or more other individual incubators such at least two of the individual incubators are being operated in parallel with respect to the atmospheric conditions within the individual incubators. In particular embodiments, all of the individual incubators 20 are operated in parallel with respect to the atmospheric conditions throughout a cell culture duration or workflow.

Operating individual incubators 20 (within a cell culture system 10, as provided herein) in parallel may be advantageous when scaling up a cell culture workflow in which the optimal atmospheric conditions have already been determined. A cell culture workflow may occur in an experimental context or in a manufacturing context. Merely by way of example, a manufacturing context may be a process that is directed toward production of a cell population for clinical use, or for harvesting of a cell-derived product. In a clinical manufacturing context, medical use medical grade gases may be appropriate. The scope of embodiments of the systems and methods as provided herein, may further include medical grade gas mixtures.

In some embodiments of a method of controlling the atmospheric conditions of two or more multiple incubators 20, the method includes operating at least two of the individual incubators operate in parallel with respect to the atmospheric conditions within the individual incubators, and further includes assaying an effect of a bioactive agent within the cell populations incubating, respectively in the two or more incubators.

By way of example, the bioactive agent may a cytotoxic or potentially cytotoxic drug, wherein the drug has an observable toxic effect on one or more parameters of cell culture performance. By way of another example, the bioactive agent may have an effect on an expression of cellular phenotype, and wherein cellular phenotype comprises any aspect of cell culture performance or any observable aspect of cellular function.

In some embodiments of a method of controlling the atmospheric conditions of two or more multiple individual incubators 20, the method includes operating each of the incubators independently of the one or more other individual incubators such that at least one of the individual incubators differs from at least one other individual incubator with respect to the atmospheric conditions within the individual incubators over the course of a culture duration or workflow. Operating individual incubators 20 within a system such that atmospheric conditions vary, particularly in a systematic manner, may be advantageous when testing atmospheric conditions to achieve a desirable cell culture performance, and thereby determine favorable or optimal atmospheric conditions for that particularly desired cell culture performance.

In some embodiments of a method of controlling the atmospheric conditions of two or more multiple incubators 20, regulating oxygen level and total gas pressure within at least two of the more or more individual incubators includes regulating at least two of the two or more individual incubators such that the atmospheric conditions in the at least two incubators differ with respect to at least one of the oxygen level or total gas pressure; the method may further include comparing one or more parameters of cell culture performance under the differing atmospheric conditions. A parameter of cell culture performance includes any one or more of cell growth rate, death rate, achievable cell density, rate of production of a cell product, cell morphology, cell dimension, cell adherent properties, cell electrical properties, cell metabolic activity, cell migratory behavior, cell activation state, or any other observable aspect of cellular function.

In some embodiments of the method, comparing one or more parameters of cell culture performance under the differing atmospheric conditions may include evaluating an effect of a bioactive agent or drug on one or more parameters of cell culture performance. Such an effect may be considered positive or negative. For example, a parameter appropriate for a cytotoxic drug or biologic may be that of killing or damaging a targeted cell type, in which case a potency titration of the effect of the drug can be demonstrated by varying the dose of the drug within a group of cell culture vessels.

In some embodiments of the method, comparing one or more parameters of cell culture performance under the differing atmospheric conditions may further include identifying the atmospheric conditions that optimize a manifestation of the one of more desired parameters of cell culture performance.

Some embodiments of a method of culturing cells within two or more individual incubators 20 of cell culture incubator system 10 may occur in a system embodiment in which at least one of the two or more incubators includes an analytic module 52 within its integrated controller system 40.

Some embodiments of a method of culturing cells within two or more individual incubators 20 of a cell culture incubator system 10 may occur in a system embodiment in which at least one of the two or more incubators includes an impedance mapping module 56-I configured to receive grid site-tagged impedance data transmitted from an electrode mapping grid included within a cell culture surface of the cell culture vessel positioned within the cell culture incubator. In such a cell culture system 10 embodiment, the method may further include monitoring the cells being cultured by way of mapped impedance data.

Some embodiments of a method of culturing cells within two or more individual incubators 20 of a cell culture incubator system 10 may occur in a system embodiment in which at least one of the two or more incubators includes an optical mapping module 56-O configured to receive grid site-tagged optical data transmitted from an optical mapping grid included within a cell culture surface of the cell culture vessel positioned within the cell culture incubator. In such a cell culture system 10 embodiment, the method may further include monitoring the cells being cultured by way of mapped optical data. By way of example, monitoring the cells optically may include monitoring cells with fluorescent imaging. By way of further example, monitoring the cells with fluorescent imaging may include monitoring any of antibody internalization, reporter gene assays, or immunocytochemistry.

Some embodiments of a method of culturing cells within two or more individual incubators 20 of a cell culture incubator system 10 may occur in a system embodiment in which at least one of the two or more incubators a current delivery module 54 configured to transmit electrical current by way of an electrode array disposed within a cell culture surface of the cell culture vessel positioned within the cell culture incubator. In such a cell culture system 10 embodiment the method may include transmitting current that sufficient to electroporate a cell adhering to the cell culture surface.

Cells from any common source of cells may be appropriate for culturing by the provided method; by way of particular examples, such cell populations, merely by way of example, may include a population of any of an immune cell population, a tumor cell population, or a stem cell population.

Some embodiments of a method of culturing cells within two or more individual incubators 20 of multi-incubator cell culture system 10 may further include monitoring a performance of the cultured cell population within a cell culture vessel retrospectively or in real time. Monitoring of cell culture performance may take the form of viewing direct data readouts, as provided by embodiments of cell culture system 10 display, as well as in the form of exportable data sets that can be analyzed in further spreadsheets and more complex process analysis databases. Data are typically reported in the form of tables and charts, such charts, for example, showing a chronological view of data or an X-Y or X-Y-Z scatter plot of data, for visualization, analysis, and understanding.

Examples of cell culture performance may include any of the cell population growth rate, the cell population death rate, morphology of cells within the population, cell size distribution within the population, level of cell clustering within the population, level of production of a cellular product, or pH of the cell culture medium. In particular embodiments, monitoring the performance of the cultured cell population is done non-invasively, without physical invasion of an instrument into a space within the cell culture vessel.

As noted above, cell populations being cultured within a workflow in separate individual incubators within multi-incubator cell culture system 10 need not be derived from a common seeding source, they may be derived from different seeding sources. Accordingly, some embodiments of the provided technology include a method of culturing two or more cell populations within two or more individual incubators of a multi-incubator cell culture system 10, wherein each individual incubator 20 is capable of controlling internal atmospheric conditions independently of the internal atmospheric conditions in the other one or more incubators. Embodiments of this method include seeding cells from the from two or more cell populations into two or more individual cell culture vessels, incubating the two or more seeded cell culture vessels, respectively, in the two or more individual incubators, and controlling the atmospheric conditions in each of the individual incubators independently by way of a single integrated cell culture controller system that is operably linked to the each of the individual incubators.

Particular Embodiments of the Technology

A number of embodiments of the technology, a multi-incubator cell culture system 10 with multiple gas flow regulation capabilities that allow high resolution control of low oxygen and high-pressure conditions gaseous conditions, further include various cell monitoring and functional interventional capabilities as described herein. Examples of cell monitoring capabilities include optical monitoring and impedance-based monitoring; interventional capabilities include electroporation.

These embodiments, as described below, may apply to any one or more individual incubator within a multi-incubator cell culture system 10; these embodiments may also refer to a single stand-alone cell culture incubator. Several enumerated embodiments are as follows:

1. a cell culture incubator configured for impedance-based cell monitoring capability,
2. a cell culture incubator configured for optical monitoring capability,
3. a cell culture incubator configured for both impedance-based monitoring and optical monitoring capability,
4. a cell culture incubator configured for electroporation capability,
5. an incubator configured for both impedance monitoring and electroporation capabilities, 6. an incubator configured for both optical monitoring and electroporation capabilities,
7. an incubator configured for impedance monitoring, optical monitoring, and electroporating capabilities.

Each of these embodiments is summarized below. Embodiments of the technology further include any combination of features described in the context of any one particular embodiment with any other embodiment described herein.

1. Incubator with Impedance-Based Cell Monitoring

In one embodiment of the technology, a cell culture incubator is configured to monitor cells in culture by way of impedance measurements. According, a cell culture incubator includes an enclosed environmental chamber; and integrated controller system operably communicative with the enclosed environmental chamber, the integrated controller system configured to regulate an oxygen level and a total gas pressure within the enclosed environmental chamber, wherein the oxygen level and the total gas pressure are regulated independently of each other. The integrated controller system includes an impedance mapping module configured to receive mapped impedance data transmitted from an electrode-based mapping grid, the mapping grid included within a cell culture surface of a cell culture vessel, the vessel housed within the cell culture incubator. The mapped impedance data are processable into a map of cellular attachment to the cell culture surface of the cell culture vessel. The mapped impedance data are typically obtained in a manner non-invasive of the cell culture vessel. A cell culture vessel may be any conventional cell culture accommodation, of any scale, including merely by way of example, a cell culture plate, a cell culture dish, a cell culture well, a cell culture cartridge, a cell culture flask, or a cell culture bag.

In some embodiments, the mapped impedance data are resolvable to a cell culture surface site having a diameter approximately equivalent to a diameter of a single cell attached to the surface of the cell culture vessel. In some embodiments, the mapped impedance data are locatable to an X-Y axis identified site on the cell culture surface of the cell culture vessel.

In some of these method embodiments, impedance data are resolvable to a site having a diameter approximately equivalent to that of the diameter of a single cell attached to the surface of the cell culture vessel. In such embodiments, by tracking a location of a single cell over time, a movement rate of a single cell is derivable. In a related embodiment, by tracking a location of a sufficient number of individual cells over time, a statistical profile of the movement rate of a population of cells across the cell culture surface is derivable.

In some embodiments of a cell culture incubator, mapped impedance data are transmitted from the cell culture vessel to the impedance mapping module. In some of these embodiments or modes of operation, mapped impedance data are transmitted from the cell culture vessel to the impedance mapping module in an episodic manner. In other embodiments or modes of operation, the mapped impedance data are transmitted from the cell culture vessel to the impedance mapping module in a continuous manner, thereby providing a real-time view of the mapped impedance data.

In some embodiments of the cell culture incubator, a map of cellular attachment to the cell culture surface is processable into a measurement of the density of cells/unit surface area of the cell culture vessel. In some embodiments, the map of cellular attachment to the cell culture surface is processable into a location of an individual single cell. In particular embodiments, wherein a cell location is being tracked over time, the map of cellular attachment to the cell culture surface is processable into a tracking of a movement of a single individual cell. And in particular embodiments, the map of cellular attachment to the cell culture surface is processable into a rate of movement of a single individual cell.

Some embodiments of the cell culture incubator further include a power source to provide electrical current to the electrode-based mapping grid. The power source may include a voltage regulator to the power source to enable regulation of voltage applied to the electrode-based mapping grid. The power source may include an amperage regulator to the power source to enable regulation of amps applied to the electrode-based mapping grid. In such embodiments, the power source is operable in a manner to deliver power in a profile appropriate for impedance-based mapping of cellular presence on the cell culture surface.

Method of Impedance-Based Cell Monitoring

Various methods by which a cell culture incubator with impedance-based monitoring capability (as described above) can be operated will now be summarized. In one embodiment, a method of impedance-based monitoring of cellular presence on a surface of a cell culture vessel includes culturing cells in a liquid culture medium, the medium being contained within a cell culture vessel, the vessel disposed within a culture incubator, receiving impedance data informative of impedance to electrical current flow between mapping electrodes disposed within the cell culture surface, tracking the impedance data over time; and processing the impedance data into a measure of a cellular presence within the cell culture vessel.

In some of these method embodiments, the impedance-based monitoring is practiced episodically; in other embodiments, the impedance-based monitoring is practiced in a substantially continuous manner. In some embodiments, the measure of cellular presence within the cell culture vessel relates to a cell density on the cell culture surface.

In some of these method embodiments, the impedance data are resolvable to a site on the cell culture surface with a diameter as low as 300 microns. In other embodiments, the impedance data are resolvable to a site with a diameter as low as 100 microns; in still further embodiments, the impedance data are resolvable to a site with a diameter as low as 50 microns.

In some of these method embodiments, impedance data are resolvable to a site having a diameter approximately equivalent to that of the diameter of a single cell attached to the surface of the cell culture vessel. In such embodiments, by tracking a location of a single cell over time, a movement rate of a single cell is derivable. In a related embodiment, by tracking a location of a sufficient number of individual cells over time, a statistical profile of the movement rate of a population of cells across the cell culture surface is derivable.

In various embodiments of the method, the cellular presence, per processed impedance data may refers to either to cell presence in terms of the number of cells or in terms of the strength of adherence of cells to the surface. Accordingly, in some embodiments, the measure of cellular presence within the cell culture vessel relates to a cell density on the cell culture surface (i.e., the number of cells/unit surface area). In other embodiments, the measure of cellular presence relates to a level of adherence of the cultured cells to the cell culture surface. For example, the level of adherence of the cultured cells to the cell culture surface may be processed into a value representative of a cumulative result of all cells within a given unit surface area. In another example, the level of adherence to the cell culture surface can be normalized to a measure of cell density per unit surface area, thereby providing a measure of the specific level of adherence per cell.

Measuring the cellular presence on a cell culture surface can permit the development of assays to measure the effects of bioactive agents that either enhance or diminish cellular presence. Accordingly, in some embodiments, the method may further include measuring the effect of a bioactive agent on the measure of cellular presence within the cell culture vessel. For example, a bioactive agent may affect a cell density value (number of cells/unit surface area) on the cell culture surface. In another example, the bioactive agent may affect a level of the cell adherence to cell culture surface. It is anticipated that the effect of a bioactive agent on cell adherence may be evident more quickly than cell density. In a particular example, the method may be applied to candidate drugs being tested for effective toxicity against cancer cells.

2. Incubator with Optical Monitoring

In one embodiment of the technology, a cell culture incubator includes a capability to optically monitor cells being cultured therein. Accordingly, a cell culture incubator includes an enclosed environmental chamber; and an integrated controller system operably communicative with the enclosed environmental chamber, the integrated controller system is configured to regulate an oxygen level and a total gas pressure within the enclosed environmental chamber, wherein the oxygen level and the total gas pressure are regulated independently of each other. The integrated controller system includes an optical mapping module configured to receive optical mapping grid site-tagged optical data transmitted from an optical mapping grid, the optical mapping grid included within a cell culture surface of a cell culture vessel housed within the cell culture incubator. The mapped optical data are processable into a map of cellular presence on the cell culture surface of the cell culture vessel.

In various embodiments, the mapped optical data may include optical phase contrast data, bright field data, or fluorescence data. In some embodiments, the cell culture incubator may further include optical imaging hardware, such as CCD (charge-coupled device) or CMOS (complementary metal oxide semiconductor) based detection technology.

In some embodiments, the integrated controller system is configured to receive mapped optical data that are transmitted from the cell culture vessel to the optical mapping module in an episodic manner. In some embodiments, the integrated controller system is configured to receive mapped optical data that are transmitted from the cell culture vessel to the optical mapping module in a continuous manner, thus allowing optical data to be processed and delivered in real time.

Method of Optical Detection and Tracking

Various methods by which a cell culture incubator with optical monitoring capability (as described above) can be operated will now be summarized. Accordingly, a method of optically monitoring cells on a cell surface of a cell culture vessel includes culturing cells in a liquid culture medium, the medium being contained within a cell culture vessel, and the vessel being disposed within a cell culture incubator. The method further includes receiving optical data transmitted from the optical mapping grid within the cell culture surface, and processing the transmitted optical data into a map of cellular presence across the cell culture surface.

In some embodiments of the method, optically monitoring cells may be practiced episodically, and in some embodiments, optically monitoring cells may be practiced in a substantially continuous manner, thereby enabling real-time optical monitoring of cells in culture.

In some embodiments of the method, processing the transmitted optical data into a map of cellular presence across the cell culture surface includes yielding processed data that relate to a cell density per unit surface area on the cell culture surface. In some embodiments of the method, processing the transmitted optical data into a map of cellular presence across the cell culture surface includes yielding processed data that relate to a cell density per unit medium volume in the cell culture vessel.

In some embodiments of the method, processing the transmitted optical data into a map of cellular presence across the cell culture surface includes yielding processed data that are resolvable to a site having a diameter approximately equivalent to the diameter of a single cell attached to the surface of the cell culture vessel. In such embodiments, by tracking a location of a single cell over time, a movement rate of a single cell is derivable. And in other embodiments that are able to track a location of a single cell over time, by tracking a location of a sufficient number of individual cells over time, a statistical profile of the movement rate of a population of cells across the cell culture surface is derivable.

3. Incubator with Both Impedance-Based Cell Monitoring and Optical Monitoring Capabilities In one embodiment of the technology, a cell culture incubator includes both (1) impedance-based cell monitoring capability and (2) optical monitoring capability to monitor cells being cultured therein. Accordingly, a cell culture incubator includes an enclosed environmental chamber; and an integrated controller system operably communicative with the enclosed environmental chamber, the integrated controller system is configured to regulate an oxygen level and a total gas pressure within the enclosed environmental chamber, wherein the oxygen level and the total gas pressure are regulated independently of each other. The integrated controller system includes both an impedance mapping module and an optical mapping module.

The impedance module is configured to receive mapped impedance data transmitted from an electrode-based mapping grid, the mapping grid included within a cell culture surface of a cell culture vessel, the vessel housed within the cell culture incubator. The mapped impedance data are processable into a map of cellular attachment to the cell culture surface of the cell culture vessel.

The optical mapping module is configured to receive optical mapping grid site-tagged optical data transmitted from an optical mapping grid, the optical mapping grid included within a cell culture surface of a cell culture vessel housed within the cell culture incubator. The mapped optical data are processable into a map of cellular presence on the cell culture surface of the cell culture vessel.

Method of Impedance-Based and Optical Detection and Tracking of Cells

Various methods by which a cell culture incubator with impedance-based monitoring capability and optical monitoring capability (as described above) can be operated will now be summarized. Accordingly, a method of monitoring of cellular presence on a surface of a cell culture vessel includes culturing cells in a liquid culture medium, the medium being contained within a cell culture vessel, and the vessel disposed within a culture incubator. The method further includes both receiving impedance data informative of impedance to electrical current flow between mapping electrodes disposed within the cell culture surface and receiving optical data transmitted from the optical mapping grid within the cell culture surface. The method further includes both processing the impedance data into an electrical measure of cellular presence, and processing the optical data into an optical measure of cellular presence.

4. Incubator with Electroporation Capability

In one embodiment of the technology, a cell culture incubator includes a capability to electroporate cells being cultured therein, electroporation referring to a particular method of transfection, wherein bioactive agents are allowed entry from a liquid cell medium into the cultured cells. Accordingly, a cell culture incubator includes an enclosed environmental chamber; and an integrated controller system operably communicative with the enclosed environmental chamber, the integrated controller system being configured to regulate an oxygen level and a total gas pressure within the enclosed environmental chamber, wherein the oxygen level and the total gas pressure are regulated independently of each other. The integrated controller system includes a current delivery module configured to transmit electrical current by way of an electrode array disposed within a cell culture surface of a cell culture vessel, the cell culture vessel housed within the cell culture incubator. The transmitted current is sufficient and effective to electroporate a cell adhering to the cell culture surface, and the cell, once electroporated, allows the entry of a bioactive agent from a liquid medium into the cell.

Method of Electroporation

Various methods by which a cell culture incubator with electroporating capability (as described above) can be operated will now be summarized. Accordingly, a cell culture incubator with an electroporating capability may be directed toward a method of electroporating cells that are adhering to a cell culture surface of a cell culture vessel. Such a method includes culturing cells in a liquid culture medium, the medium being contained within a cell culture vessel, the vessel disposed within a cell culture incubator as above. The method further includes transmitting electrical current from the current delivery module of the cell culture incubator to an array of electroporating electrodes disposed within the cell culture surface of the cell culture vessel, the transmitted current being of sufficient voltage, amperage, and duration to electroporate a cell adhering to the cell culture surface. wherein a cell, once electroporated, allows the entry of a bioactive agent from a liquid medium into the cell. A bioactive agent is any agent that has an effect on the biology of cells being cultured in the described incubator. In some embodiment of the method, the transmitted current is also sufficient to electroporate a cell in suspension, not adhering to the cell culture surface.

In some embodiments of a method of electroporating cells, the bioactive agent is a nucleic acid, such as DNA or RNA, in any of a variety of forms and with any of a variety of biological effects, as described further below.

In some embodiments, the nucleic acid bioactive agent includes a DNA molecule, which may, merely by way of example, be in the form of a linear DNA molecule, a circular DNA molecule, a supercoiled DNA molecule, or an epigenetically modified DNA molecule. In particular embodiments, the DNA molecule is a naked DNA molecule, the naked DNA molecule being so-called by being unaccompanied by any of a protein or a lipid moiety. In a particular embodiment, the DNA molecule encodes a chimeric antigen receptor. In some of these embodiments, the chimeric antigen receptor, when expressed as a protein within the host cell, becomes inserted into a host cell membrane.

In some embodiments, the nucleic acid bioactive agent includes a DNA molecule, the method further comprising the DNA expressing transiently as RNA or transiently as protein. In some embodiments, however, the nucleic acid bioactive agent includes a DNA molecule, and the delivery the DNA results in integration of at least of portion of the delivered DNA into the genome of the host cell. In some of these embodiments, the integration of at least of portion of the delivered DNA includes a transduction of the host cell in that the integrated DNA is operably expressible. In some of these embodiments, the genomically-integrated DNA is expressed by way of transcription into RNA. In various embodiments, the genomically-integrated DNA is expressed by way of translation into protein, or by way of affecting flux through a metabolic pathway. In other embodiments, the DNA is not integrated into the genome of the host cell and is expressed transiently by way of any of transcription into RNA, translation into protein, or by way of affecting flux through a metabolic pathway.

In some embodiments, the nucleic acid bioactive agent includes an RNA molecule, which, by way of example, may include of siRNA, mRNA, miRNA, lncRNA, tRNA, shRNA, or self-amplifying mRNA. In particular examples, the introduction of the RNA molecule results in expression of a protein within the target cell, and in some examples, the nucleic acid expression is evident by way of affecting metabolite flux through a cellular metabolic pathway.

In some electroporation directed methods, an electroporated bioactive agent is a protein or a peptide. Merely by way of example, a protein or peptide can be any of an antibody, an enzyme, or a transcription factor. The protein or peptide may also be tagged with any useful tag, such as a fluorescent tag.

In various electroporation directed methods, the bioactive agent may include a lipid moiety. The bioactive agent may be particulate in character, such as a nanoparticle. The bioactive agent may include a Cas9 protein and a guide RNA or donor DNA. The bioactive agent may include a nucleic acid encoding for a Cas9 protein and a guide RNA or donor DNA. The bioactive agent may also a virus.

In some embodiments of the method, electroporation is a first method of transfection, but the method further includes using a second method of transfection in conjunction with electroporation. Such second transfective method may include any known method of transfection, including, merely by way example, lipofection, calcium phosphate transfection, chemical transfection, polymer transfection, gene gun, magnetofection, and sonoporation.

In some embodiments of the method, electroporation is a first method of transfection, but the method further includes using a second method of transfection in conjunction with electroporation, the second method including regulating each of a total gas pressure and an oxygen level within the incubator independently of each other and independently of ambient external gaseous conditions.

5. Incubator with Both Impedance-Based Cell Monitoring and Electroporating Capabilities In one embodiment of the technology, a cell culture incubator with both impedance-based cell monitoring and electroporating capabilities is provided. Accordingly, a cell culture incubator includes an enclosed environmental chamber and a an integrated controller system operably communicative with the enclosed environmental chamber. The integrated controller system is configured to regulate an oxygen level and a total gas pressure within the enclosed environmental chamber, the oxygen level and the total gas pressure being regulated independently of each other. The integrated controller system includes an impedance mapping module configured to receive mapped impedance data transmitted from an electrode-based mapping grid, the mapping grid being included within a cell culture surface of a cell culture vessel, the vessel being housed within the cell culture incubator. The mapped impedance data are processable into a map of cellular attachment to the cell culture surface of the cell culture vessel. The integrated controller system includes a current delivery module configured to transmit electrical current by way of an electrode array disposed within a cell culture surface of a cell culture vessel, the cell culture vessel being housed within the cell culture incubator, the transmitted current being effective to electroporate a cell adhering to the cell culture surface.

Method of Impedance-Based Cell Monitoring and Electroporating

Various methods by which a cell culture incubator that includes impedance-based cell monitoring and electroporating capabilities (as described above) can be operated will now be summarized. Accordingly, a method of monitoring of cellular presence on a surface of a cell culture vessel includes culturing cells in a liquid culture medium, the medium being contained within a cell culture vessel, the vessel being disposed within a culture incubator. The method further includes receiving impedance data informative of impedance to electrical current flow between mapping electrodes disposed within the cell culture surface, and transmitting electrical current from the current delivery module of the cell culture incubator to the array of electroporating electrodes disposed within the cell culture surface of the cell culture vessel, the transmitted current being sufficient to electroporate a cell adhering to the cell culture surface, wherein cell, once electroporated, allows the entry of a bioactive agent from a liquid medium into the cell.

6. Incubator with Both Optical-Based Cell Monitoring and Electroporating Capabilities In one embodiment of the technology, a cell culture incubator with both optical-based cell monitoring and electroporating capabilities is provided. Accordingly, a cell culture incubator including an enclosed environmental chamber and an integrated controller system operably communicative with the enclosed environmental chamber, wherein the integrated controller system is configured to regulate an oxygen level and a total gas pressure within the enclosed environmental chamber, and wherein the oxygen level and the total gas pressure are regulated independently of each other. The integrated controller system includes an optical module configured to receive mapped optical data transmitted from an optical mapping grid, the mapping grid being included within a cell culture surface of a cell culture vessel, and the vessel being housed within the cell culture incubator. The mapped optical data are processable into a cellular presence on the cell culture surface of the cell culture vessel. The integrated controller system includes a current delivery module configured to transmit electrical current by way of an electrode array disposed within a cell culture surface of a cell culture vessel, the cell culture vessel being housed within the cell culture incubator, wherein the transmitted current is effective to electroporate a cell adhering to the cell culture surface.

Method of Optical Based Cell Monitoring and Electroporating

Various methods by which a cell culture incubator that includes optical-based cell monitoring and electroporating capabilities (as described above) can be operated will now be summarized. Accordingly, a method of monitoring of cellular presence on a surface of a cell culture vessel includes culturing cells in a liquid culture medium, the medium being contained within a cell culture vessel, the vessel being disposed within a culture incubator. The method further includes receiving optical data transmitted from the optical mapping grid within the cell culture surface, and transmitting electrical current from the current delivery module of the cell culture incubator to the array of electroporating electrodes disposed within the cell culture surface of the cell culture vessel, the transmitted current being sufficient to electroporate a cell adhering to the cell culture surface, wherein cell, once electroporated, allows the entry of a bioactive agent from a liquid medium into the cell.

7. Incubator with (a) Impedance-Based Monitoring, (b) Optical Monitoring, and (c) Electroporating Capabilities In one embodiment of the technology, a cell culture incubator includes (1) impedance-based cell monitoring capability, (2) optical monitoring capability to monitor cells being cultured therein, and (3) a capability to electroporate cells being cultured therein. Accordingly, a cell culture incubator includes an enclosed environmental chamber, and an integrated controller system operably communicative with the enclosed environmental chamber, the integrated controller system being configured to regulate an oxygen level and a total gas pressure within the enclosed environmental chamber, the oxygen level and the total gas pressure being regulated independently of each other.

In such embodiments, the integrated controller system includes (a) an impedance mapping module configured to receive mapped impedance data transmitted from an electrode-based mapping grid, the mapping grid included within a cell culture surface of a cell culture vessel, the vessel housed within the cell culture incubator, (b) an optical mapping module configured to receive optical mapping grid site-tagged optical data transmitted from an optical mapping grid, the optical mapping grid included within a cell culture surface of a cell culture vessel being housed within the cell culture incubator, and (c) a current delivery module configured to transmit electrical current by way of an electrode array disposed within a cell culture surface of a cell culture vessel, the cell culture vessel being housed within the cell culture incubator.

Various methods by which a cell culture incubator that includes impedance-based cell monitoring, optical-based cell monitoring, and electroporating capabilities (as described above) can be operated will now be summarized. Accordingly, a method of monitoring of cellular presence on a surface of a cell culture vessel includes culturing cells in a liquid culture medium, the medium being contained within a cell culture vessel, the vessel being disposed within a culture incubator. The method further includes receiving impedance data informative of impedance to electrical current flow between mapping electrodes disposed within the cell culture surface, as well as receiving optical data transmitted from the optical mapping grid within the cell culture surface. The method further includes transmitting electrical current from the current delivery module of the cell culture incubator to the array of electroporating electrodes disposed within the cell culture surface of the cell culture vessel, the transmitted current being sufficient to electroporate a cell adhering to the cell culture surface, wherein cell, once electroporated, allows the entry of a bioactive agent from a liquid medium into the cell.

Any one or more features or steps of any embodiment of the technology disclosed herein (device or method) can be combined with any one or more other features of any other embodiment of the technology, without departing from the scope of the described technology. It should also be understood that the technology is not limited to the embodiments that are described or depicted herein for purposes of exemplification, but are to be defined only by a fair reading of claims appended to the patent application, including the full range of equivalency to which each element thereof is entitled. Some theoretical considerations of the inventors have been advanced in this application, as, for example, regarding the biological effects of oxygen level and atmospheric pressure on cells. These theoretical considerations are offered strictly for the purpose of conveying concepts underlying the described technology, not to support any of the claims, all of which stand wholly independent of any theoretical considerations.

What is claimed is:

1. A cell culture incubator system comprising: two or more individual incubators, wherein each individual incubator comprises an environmental chamber; a first set of one or more sensor modules; a second set of one or more sensor modules; and an atmospheric regulation system configured to regulate atmospheric conditions within the environmental chamber of each individual incubator independent of other individual incubators, the atmospheric conditions comprising an oxygen level and a total gas pressure, wherein the oxygen level and the total gas pressure are regulated independently of each other in each of the individual incubators, wherein the atmospheric regulation system comprises an integrated controller system configured to command atmospheric regulation of each of the individual incubators independently of the other individual incubators, and wherein the integrated controller system comprises: a single master controller operably linked to each of the individual incubators; and two or more subcontrollers, each subcontroller dedicated, respectively, to one of the two or more individual incubators, wherein the master controller is configured to deliver a command comprising an atmospheric condition set point to each of the two or more subcontrollers, wherein each subcontroller regulates the atmospheric regulation system of the individual incubator to which it is dedicated, in accordance with the atmospheric condition set point commands of the master controller, and wherein the master controller is configured to exert direct operational control over at least one of the individual incubators independently of the subcontrollers, wherein the first set of one or more sensor modules within each individual incubator is in communication with only the subcontroller dedicated to that individual incubator and are not in direct communication with the master controller;

wherein the second set of one or more sensor modules within each individual incubator is in direct communication with only the master controller and are not in communication with the subcontroller dedicated to that individual incubator; and wherein the master controller is configured to receive environmental condition data directly from the second set of one or more sensor modules without any intermediate computing device disposed between the master controller and the second set of one or more sensor modules.

2. The cell culture incubator system of claim 1, wherein each of the two or more subcontrollers is positioned within the incubator to which it is dedicated and wherein the second set of one or more sensor modules is positioned within the incubator.

3. The cell culture incubator system of claim 1, wherein each subcontroller comprises two or more atmospheric condition regulation modules, said modules comprising an oxygen module and a pressure module.

4. The cell culture incubator system of claim 3, wherein each subcontroller comprises one or more further atmospheric condition regulation modules, said further modules comprising a carbon dioxide module, a temperature module, or a humidity module.

5. The cell culture incubator system of claim 1, wherein the master controller is configured to request and receive sensor data from any of the two or more subcontrollers, said sensor data comprising data from any sensed atmospheric condition from any of the two or more individual incubators.

6. The cell culture incubator system of claim 5, wherein the master controller, in response to the sensor data received from any of the two or more subcontrollers, is configured to send atmospheric regulation commands to an atmospheric regulation module within any of the two or more individual incubators.

7. The cell culture incubator system of claim 1, wherein the integrated controller system is configured to command two or more of the individual incubators in parallel with respect to the atmospheric conditions within the individual incubators.

8. The cell culture incubator system of claim 1, wherein the integrated controller system being configured to operate each of the individual incubators independently of the other individual incubators and is configured to command the individual incubators such that at least one of the individual incubators differs from at least one other individual incubator with respect to the atmospheric conditions within the individual incubators.

9. The cell culture incubator system of claim 1, wherein the integrated controller system comprises an oxygen module and a pressure module, and wherein the atmospheric regulation system further comprises: an oxygen sensor configured to measure the oxygen level within the environmental chamber and to convey an oxygen signal to the oxygen module; a pressure sensor configured to measure the total gas pressure within the environmental chamber and to convey a pressure level signal to the pressure module; a gas flow system comprising multiple gas sources flowably connected to the environmental chamber, said gas sources comprising a nitrogen source, a carbon dioxide source, and an air source, wherein gas flow from each source is regulated by the integrated controller system; and wherein the integrated controller system is configured to: a) provide a hypoxic oxygen set point to the oxygen module; b) provide a hyperbaric total gas pressure set point to the atmospheric regulation system, wherein the regulation of the oxygen level to the hypoxic set point prevails despite an oxygen partial pressure-increasing effect of the hyperbaric pressure condition, per the hyperbaric total gas pressure set point.

10. The cell culture incubator system of claim 1, wherein the master controller is configured such that when an atmospheric condition within an environmental chamber of one of the individual incubator is sensed as being out of compliance with the atmospheric condition set point, the master controller drives a transition of the atmospheric condition within the environmental chamber toward the atmospheric condition set point, said transition mediated by the subcontroller dedicated to the individual incubator.

11. The cell culture incubator system of claim 9, wherein when an atmospheric condition within an environmental chamber of one of the individual incubators is sensed as being in-compliance with the atmospheric condition set point, the subcontroller dedicated to the individual incubator is operable to control the gas flow system without an ongoing atmospheric set point command from the master controller.

12. The cell culture incubator system of claim 1, wherein each of the individual incubators comprises at least two atmospheric sensors, said at least two atmospheric sensors comprising an oxygen sensor and an atmospheric pressure sensor, said at least two atmospheric sensors disposed within the environmental chamber, said at least two atmospheric sensors configured to transmit sensed data collected by the at least two atmospheric sensors to a subcontroller of the two or more subcontrollers of the integrated controller system.

13. The cell culture incubator system of claim 12, wherein the subcontroller of the integrated controller system is configured to transmit the sensed data to the master controller.

14. The cell culture incubator system of claim 13, wherein the subcontroller of the integrated controller system is configured to transmit the sensed data to the master controller at a rate that is controllably variable.

15. The culture incubator system of claim 1, wherein the integrated controller system of at least one of the two or more individual incubators comprises one or more analytic modules configured to non-invasively capture analytic data informative of an aspect of performance of a cell population being cultured within a cell culture vessel disposed within the incubator.

16. The culture incubator system of claim 15, wherein the analytic module of the integrated controller system of at least one of the two or more individual incubators comprises an impedance mapping module configured to receive grid site-tagged impedance data transmitted from an electrode mapping grid included within a cell culture surface of the cell culture vessel disposed within the incubator, and wherein the mapped impedance data are processable into a map of cellular attachment to the cell culture surface of the cell culture vessel.

17. The culture incubator system of claim 15, wherein the analytic module of the integrated controller system of the at least one of the two or more individual incubators comprises an optical module configured to receive optical data captured from the cell culture vessel within the incubator, and wherein the optical data are processable into a measure of cellular presence within the cell culture vessel.

18. The culture incubator system of claim 17, wherein the optical module is configured to receive optical data that is site-tagged, said optical data transmitted from an optical mapping grid, the optical mapping grid included within a cell culture surface of the cell culture vessel disposed within the cell culture incubator, and wherein the mapped optical data are processable into a map of cellular presence on the cell culture surface of the cell culture vessel.

19. The culture incubator system of claim 1, wherein the second set of one or more sensor modules consists of an optical sensor and an impedance sensor.

20. A method of controlling two or more cell culture incubators each connected to a master controller, comprising delivering atmospheric condition set point commands to two or more subcontrollers of the master controller, wherein each subcontroller is associated with a cell culture incubator of the two or more cell culture incubators, and wherein each of the two or more subcontrollers regulates an atmospheric regulation system of the individual incubator to which it is associated in accordance with the atmospheric condition set points commands of the master controller, wherein the atmospheric regulation system is configured to regulate atmospheric conditions within a environmental chamber of each individual incubator, wherein the atmospheric conditions comprise an oxygen level and a total gas pressure, wherein the oxygen level and the total gas pressure are regulated independently of each other in each individual incubator, and wherein one or more sensor modules within each individual incubator is in direct communication with the master controller and are not in communication with the subcontroller dedicated to that individual incubator; and wherein the master controller is configured to receive environmental condition data directly from the one or more sensor modules without any intermediate computing device disposed between the master controller and the one or more sensor modules.

21. The method of claim 20, wherein the master controller is configured such that when an atmospheric condition within an environmental chamber of one of the individual incubator is sensed as being out of compliance with the atmospheric condition set point, the master controller drives a transition of the atmospheric condition within the environmental chamber toward the atmospheric condition set point, said transition mediated by the subcontroller dedicated to the individual incubator.

22. A cell culture incubator system comprising: two or more individual incubators, wherein each individual incubator comprises an environmental chamber, a first set of one or more sensor modules; a second set of one or more sensor modules and an atmospheric regulation system, wherein the atmospheric regulation system comprises an integrated controller system configured to command atmospheric regulation of each of the individual incubators independently of the other individual incubators, wherein the integrated controller system of at least one of the two or more individual incubators comprises one or more analytic modules configured to non-invasively capture analytic data informative of an aspect of performance of a cell population being cultured within a cell culture vessel disposed within the incubator, wherein the analytic module of the integrated controller system of at least one of the two or more individual incubators comprises an impedance mapping module configured to receive grid site-tagged impedance data transmitted from an electrode mapping grid included within a cell culture surface of the cell culture vessel disposed within the incubator, and wherein the mapped impedance data are processable into a map of cellular attachment to the cell culture surface of the cell culture vessel, and wherein the integrated controller system comprises: a single master controller operably linked to each of the individual incubators; and two or more subcontrollers, wherein each subcontroller is operably linked to one of the two or more individual incubators, wherein the first set of one or more sensor modules within each individual incubator is in communication with only a subcontroller operably linked to that individual incubator and are not in direct communication with the master controller, wherein the second set of one or more sensor modules within each individual incubator is in direct communication with only the master controller and are not in communication with the subcontroller operably linked to that individual incubator; and wherein the master controller is configured to receive environmental condition data directly from the second set of one or more sensor modules without any intermediate computing device disposed between the master controller and the second set of one or more sensor modules.

* * * * *